United States Patent
King et al.

(10) Patent No.: US 11,656,624 B2
(45) Date of Patent: May 23, 2023

(54) HORTICULTURE AIDED BY AUTONOMOUS SYSTEMS

(71) Applicant: iUNU, Inc., Seattle, WA (US)

(72) Inventors: Matthew Charles King, Seattle, WA (US); Ethan Victor Takla, Seattle, WA (US); Adam Phillip Takla Greenberg, Seattle, WA (US)

(73) Assignee: iUNU, Inc., Seattle, WA (US)

( * ) Notice: Subject to any disclaimer, the term of this patent is extended or adjusted under 35 U.S.C. 154(b) by 101 days.

(21) Appl. No.: 16/830,103

(22) Filed: Mar. 25, 2020

(65) Prior Publication Data
US 2021/0302973 A1 Sep. 30, 2021

(51) Int. Cl.
G05D 1/02 (2020.01)
G01N 33/00 (2006.01)
G01W 1/02 (2006.01)

(52) U.S. Cl.
CPC ....... G05D 1/0214 (2013.01); G01N 33/0098 (2013.01); G01W 1/02 (2013.01); G05D 2201/0201 (2013.01)

(58) Field of Classification Search
CPC ........ G05D 1/0214; G05D 2201/0201; G01N 33/0098; G01W 1/02
See application file for complete search history.

(56) References Cited

U.S. PATENT DOCUMENTS

| | | | |
|---|---|---|---|
| 10,175,362 B2 * | 1/2019 | Redden | G01N 33/0098 |
| 2014/0081479 A1 | 3/2014 | Vian et al. | |
| 2014/0089045 A1 | 3/2014 | Johnson | |
| 2016/0334276 A1 | 11/2016 | Pluvinage | |
| 2017/0032509 A1 | 2/2017 | Mannar et al. | |
| 2017/0139380 A1 | 5/2017 | Englard et al. | |
| 2018/0003656 A1 | 1/2018 | Michini et al. | |
| 2018/0264954 A1 * | 9/2018 | Lamb | G05D 1/0088 |
| 2018/0350054 A1 | 12/2018 | Fox et al. | |
| 2019/0303668 A1 | 10/2019 | King | |

(Continued)

FOREIGN PATENT DOCUMENTS

| | | | | |
|---|---|---|---|---|
| KR | 1020180087510 A | | 8/2018 | |
| KR | 1929129 B1 * | | 12/2018 | B64C 39/024 |

(Continued)

OTHER PUBLICATIONS

U.S. Appl. No. 16/830,092, filed Mar. 25, 2020, Ethan Victor Takla.

(Continued)

*Primary Examiner* — Rodney A Butler
(74) *Attorney, Agent, or Firm* — Han Santos, PLLC

(57) ABSTRACT

Techniques and examples for servicing a horticultural operation are described. A method may involve autonomously identifying the horticultural operation or a target located within the horticultural operation and an action to be performed with respect to the horticultural operation or target. The operation or target comprises at least one plant or a group of plants. Based on the identifying, a local area of the horticultural field is determined. The target is located within the local area. The target is associated to at least one autonomous vehicle. The target is located within the local area by the at least one autonomous vehicle. The action with respect to the target is performed by the at least one autonomous vehicle.

17 Claims, 16 Drawing Sheets

(56) References Cited

U.S. PATENT DOCUMENTS

| | | |
|---|---|---|
| 2019/0333195 A1 | 10/2019 | Sauder et al. |
| 2020/0019777 A1 | 1/2020 | Gurzoni, Jr. et al. |
| 2021/0004594 A1 | 1/2021 | Dai |
| 2021/0103728 A1 | 4/2021 | Young |
| 2021/0181750 A1* | 6/2021 | Gogna ................ G05D 1/0088 |
| 2021/0185886 A1* | 6/2021 | Sibley ................ A01C 21/005 |

FOREIGN PATENT DOCUMENTS

| | | |
|---|---|---|
| WO | 2018185522 A1 | 10/2018 |
| WO | 2019179270 A1 | 9/2019 |

OTHER PUBLICATIONS

International Patent Application No. PCT.US2021/023298 Search Report dated Jul. 12, 2021, 3 pages.

International Patent Application No. PCT.US2021/023298 Written Opinion dated Jul. 12, 2021, 5 pages.

International Patent Application No. PCT/US2021/023286, Search Report dated Jul. 12, 2021, 4 pages.

International Patent Application No. PCT/US2021/023286, Written Opinion dated Jul. 12, 2021, 4 pages.

U.S. Appl. No. 16/830,092, Office Action dated Jul. 25, 2022, 30 pages.

U.S. Appl. No. 16/830,092, Final Office Action dated Oct. 17, 2022, 62 pages.

\* cited by examiner

Operation Dashboard

| No. | operation ID | Crop/Plant | Field | Growing phase |
|---|---|---|---|---|
| 1 | op120 | white corn | F04 | 3 |
| 2 | op121 | rose | G02 | 2 |
| 3 | op134 | tulip | G02 | 1 |
| 4 | op222 | cabbage | F04 | 4 |
| 5 | op512 | yellow corn | F04 | 1 |
| 6 | op580 | asparagus | F03 | 3 |
| 7 | op664 | tomato | F04 | 3 |
| 8 | op670 | Fraser fir | F01 | 2 |
| 9 | op671 | Korean fir | F01 | 1 |

Local Area Map: Field F04

| | A | B | C | D | E | F | G |
|---|---|---|---|---|---|---|---|
| 1 | A1 | B1 | C1 | D1 | E1 | F1 | G1 |
| 2 | A2 | B2 | C2 | D2 | E2 | F2 | G2 |
| 3 | A3 | B3 | C3 | D3 | E3 | F3 | G3 |
| 4 | A4 | B4 | C4 | D4 | E4 | F4 | G4 |
| 5 | A5 | B5 | C5 | D5 | E5 | F5 | G5 |
| 6 | A6 | B6 | C6 | D6 | E6 | F6 | G6 |
| 7 | A7 | B7 | C7 | D7 | E7 | F7 | G7 |

Grow Operation Map: Field F04

| | A | B | C | D | E | F | G |
|---|---|---|---|---|---|---|---|
| 1 | op512 | op512 | | | | | op664 |
| 2 | op512 | op512 | | | | | op664 |
| 3 | | | | | | | |
| 4 | op120 | op120 | | | | | op664 |
| 5 | op120 | op120 | | op222 | op222 | | op664 |
| 6 | op120 | op120 | | op222 | op222 | | op664 |
| 7 | op120 | op120 | | op222 | | | |

Field Activity Map: Field F04  Date: May 22nd

| | A | B | C | D | E | F | G |
|---|---|---|---|---|---|---|---|
| 1 | | | plow soil | | | | |
| 2 | | | plow soil | | | | |
| 3 | | | | | | | |
| 4 | | | | | | | |
| 5 | | | | harvest | post-harvest clean up | | |
| 6 | | | | harvest | post-harvest clean up | | |
| 7 | | | | harvest | | | |

RZ Map: Field F04                                       Date: May 22nd

| | A | B | C | D | E | F | G |
|---|---|---|---|---|---|---|---|
| 1 | clear | clear | clear | clear | clear | restricted | clear |
| 2 | clear | clear | below 30 ft | clear | clear | restricted | clear |
| 3 | clear | clear | Obstruction 47.5405059 - 122.30454379 | clear | clear | restricted | clear |
| 4 | clear | clear | clear | clear | clear | clear | clear |
| 5 | clear | clear | clear | clear | clear | Obstruction 47.7051909 - 122.3741177 | clear |
| 6 | clear | clear | clear | clear | clear | clear | clear |
| 7 | clear | clear | clear | clear | clear | clear | clear |

FIG. 8

AV Dashboard: Field F04

May 22nd 20:00

1000

| AV ID | status | location | mission | fuel or battery level | available for mission | hydro meter | video cam | available memory | sample container | night vision camera | payload |
|---|---|---|---|---|---|---|---|---|---|---|---|
| av01 | docked, not charging | vb01 | | 98% | yes | no | yes | 14 GB | yes | yes | 10 lbs |
| av02 | docked, charging | vb01 | | 72% | yes | yes | yes | 8 GB | yes | no | 2 lbs |
| av03 | deployed, mission assigned | A4 | m10080 | 90% | no | yes | yes | 10 GB | no | no | 2 lbs |
| av04 | airborne, available for mission | G6 | | 70% | yes | yes | yes | 4 GB | no | no | 1 lb |
| av05 | docked, malfunction - mechanical | vb02 | | 85% | no | yes | yes | 32 GB | no | no | 20 lbs |
| av06 | docked, charging | vb02 | | 20% | no | yes | no | 10 GB | no | yes | 5 lbs |
| av07 | docked, charging, transferring data | vb01 | m10073 | 70% | no | no | yes | 1.2 GB | no | yes | 5 lbs |
| av08 | deployed, transferring data | E6 | m10077 | 80% | yes | no | yes | 3 GB | yes | no | 1 lb |
| av09 | docked, charging | vb01 | | 45% | yes | no | no | 8 GB | no | no | 10 lbs |
| av10 | docked, charging | vb02 | | 60% | no | yes | yes | 0.3 GB | no | yes | 5 lbs |

Mission Dashboard: Field F04

May 22nd 20:00

| entry time | mission ID | target ID | action | mission status | assignee | intended time window |
|---|---|---|---|---|---|---|
| 5/22 13:00 | m10061 | op120 | take still images | completed | av01 | 5/22 15:00 - 19:00 |
| 5/22 13:05 | m10070 | op512 | take still images | completed | av04 | 5/22 15:00 - 19:00 |
| 5/22 13:30 | m10073 | D5, D6, D7 | take still images and collect all plant-related horticultural data from field sensors | in progress | av07 | 5/22 17:00 - 19:00 |
| 5/22 13:32 | m10077 | D5, D6, D7 | take video of harvesting for 10 min | in progress | av08 | 5/22 19:30 - 20:30 |
| 5/22 19:30 | m10080 | pu_1231 | collect soil pH level | in progress | av03 | 5/22 20:00 - 21:00 |
| 5/22 19:48 | m10091 | B7 | take video while watering | to be assigned | | 5/23 05:00 - 07:00 |

FIG. 11

HORTICULTURE AIDED BY AUTONOMOUS SYSTEMS

BACKGROUND

Growers and farmers in the horticultural industry strive to enhance crop yield to maximize production and revenue. In order to achieve these objectives, horticultural tasks or actions need to increase efficiencies in planting, cultivating, and harvesting of plants. In general, these processes rely on a master grower, typically an experienced farmer, gardener, or agronomist, who oversees the horticultural tasks or actions. The master grower is usually required to physically go out to a horticultural field and spot-check sample plants in selected areas of the field. Upon examining a sample plant, the master grower may identify a horticultural status of the sample plant, such as a horticultural issue the sample plant may be having. Depending on the findings, the master grower may subsequently decide to check more plants in the neighborhood of the sample plant to determine whether the issue is a problem isolated to the sample plant or a general problem in the neighborhood. The master grower may also take measurements of environmental variables in the neighborhood to aid in determining a possible cause of the issue.

BRIEF DESCRIPTION OF THE DRAWINGS

The detailed description is described with reference to the accompanying figures, in which the left-most digit(s) of a reference number identifies the figure in which the reference number first appears. Some articles in the figures may be referenced by an alphanumeric label starting with a letter rather than a number. Such an alphanumeric label may first appear in any figure. The use of the same reference numbers or the same alphanumeric labels in different figures indicates similar or identical items.

FIG. 3 demonstrates an example operation dashboard of an AHF system.

FIG. 7 illustrates a field activity map of a horticultural field.

FIG. 8 illustrates a restricted-zone (RZ) map of a horticultural field.

FIG. 10 demonstrates an example dashboard of a horticultural field.

FIG. 11 demonstrates an example mission dashboard of a horticultural field.

DETAILED DESCRIPTION

Figure 1:
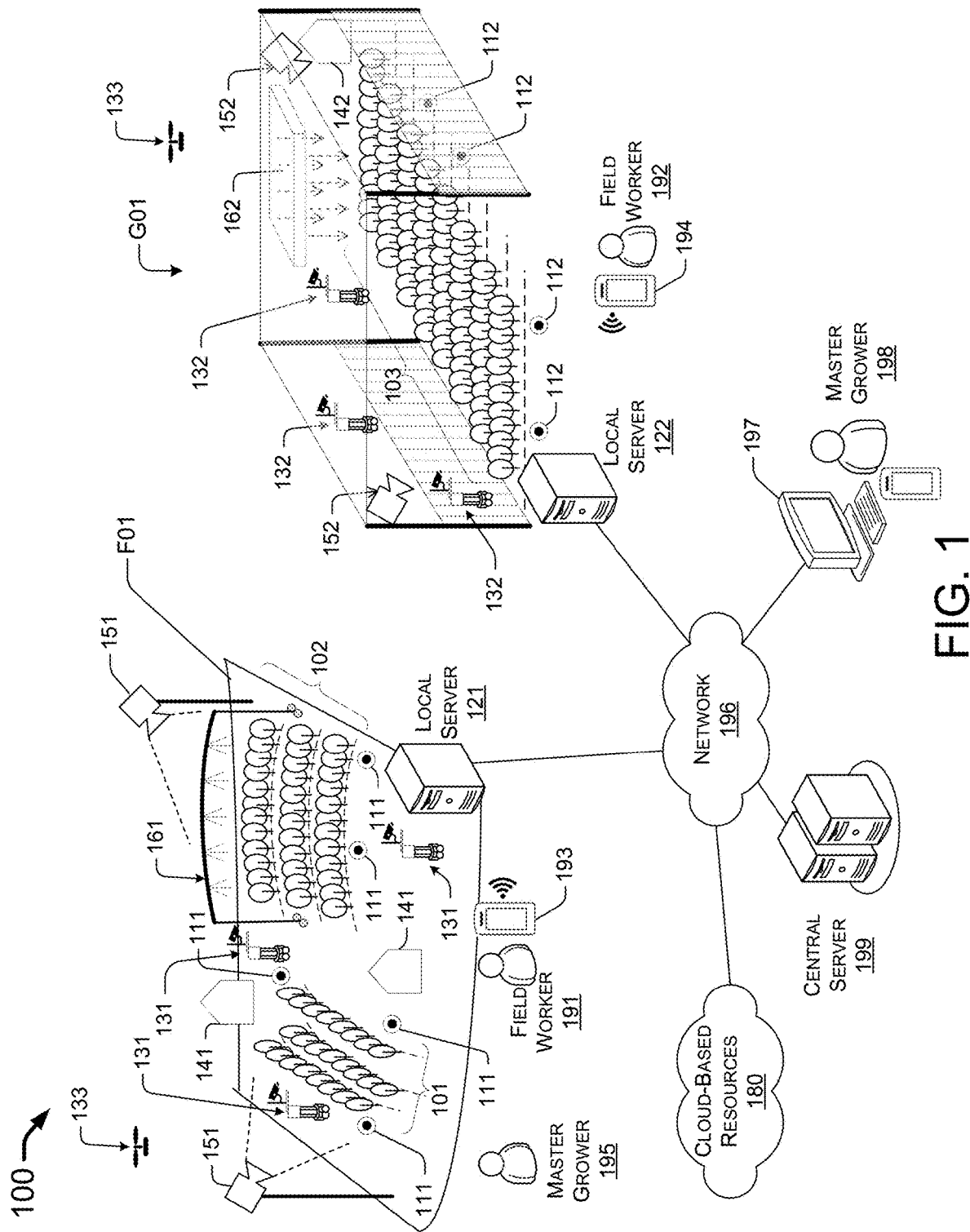
FIG. 1 illustrates a context diagram of an Autonomous Horticultural Feedback (AHF) system capable of performing an AHF process for a horticultural operation.

In order for growers and farmers in the horticultural industry to enhance crop yield and maximize production and revenue, horticultural tasks or actions often involve more than planting, cultivating, and harvesting of plants. For example, horticultural tasks or actions can include a horticultural feedback process. The horticultural feedback process includes the constant monitoring and examining of plants during various growing phases of the plants. Based on results of the monitoring or examination, early identification of any horticultural issues may be possible, and remedial solutions to address the issues may be determined and applied accordingly. The effectiveness of the remedial solutions may be assessed by further monitoring and examination of the plants after the remedial solutions are applied, thereby completing the horticultural feedback process.

In general, this process relies on a master grower, typically an experienced farmer, gardener, or agronomist, to perform the horticultural feedback process. The master grower is typically required to physically go out to a horticultural field and spot-check sample plants in selected areas of the field. Upon examining a sample plant, the master grower may identify a horticultural status of the sample plant, such as a horticultural issue the sample plant may be having. Depending on the findings, the master grower may subsequently decide to check more plants in the neighborhood of the sample plant to determine whether the issue is a problem isolated to the sample plant or a general problem in the neighborhood. The master grower may also take measurements of environmental variables in the neighborhood to aid in determining a possible cause of the issue. Accordingly, the master grower may determine one or more remedial solutions to be applied to the neighborhood to address the horticultural issue. However, the ability of the master grower or farmer to perform the described tasks is not scalable, and the master grower or farmer will be overwhelmed by the amount of tasks as the size and yield of the operation grows. This can be a limiting factor not only in the growth of operations, but in improving the efficiencies of existing operations. The horticultural feedback process can be heavily labor-intensive and time-consuming for a human master grower. The problem can be exacerbated as the physical scope of modern industrial horticultural operations become larger, often in tens or hundreds of acres. Moreover, horticultural operations within one industrial horticultural business entity may possibly encompass several horticultural fields or greenhouses that are at different geographic locations and/or exposed to different climates or growing environments. Even if a sufficient number of master growers can be resourced for performing the horticultural feedback process, inconsistency between individual master growers may compromise the effectiveness of the horticultural feedback process.

A horticultural feedback process can be used to increase yield and/or produce quality of a grow operation. Through monitoring plants of the grow operation as the plants gothrough various growing stages, horticultural problems of the grow operation may be identified, and subsequent remedial course of action may be determined and taken to address the horticultural problems.

A horticultural feedback process may include regular and periodic monitoring of a grow operation to collect horticultural data about the grow operation, which traditionally requires manual spot-checks on plants. The process is typically labor-intensive and time-consuming when executed by humans, especially if the grow operation is implemented across a large horticultural field or at multiple geographic locations. Aspects of the present disclosure address this problem. Further details are described below.

The present disclosure is directed to techniques for automating the horticultural feedback process so that human labor involvement in the process may be reduced or minimized and the process as a whole may be more efficient and/or scalable. Various embodiments described herein are generally directed to methods and systems for automatically executing horticultural tasks using autonomous devices and analysis systems that automate the analysis, diagnosis, and feedback tasks. In one example, various autonomous devices, such as robots, unmanned aerial vehicles (UAVs), together with various sensors and other data capture devices may be utilized to aid the horticultural data collection of the process.

The disclosed system automates the discovery process of potential issues in the field. For example, one or more autonomous devices can periodically (e.g., at least once a day) traverse and analyze the entirety of a growing operation, identify issues, and inform the master grower of the issues. This enables growers to scale up their operations with no upper-bound on size.

In one embodiment, methods and systems disclosed herein can automatically perform a variety of horticultural missions which aim to perform actions with respect to one or more targets (e.g., target plant 930 of FIG. 9) of a horticultural field. Target plants may be distinguished from non-target plants using sensors and other devices. A horticultural field may be divided into many local areas, and each local area may grow a certain kind of plant of some quantity. Based on an identification of the target, it can be determined which one of the many local areas the target is located within. The horticultural mission may be automatically generated based on one or more objectives that are supervised by the master grower or farmer.

In one embodiment, a particular horticultural mission may be performed by an autonomous vehicle (e.g., vehicle 920). A path (e.g., path 910) may be automatically determined so that the autonomous vehicle may travel along the path and arrive at the local area where the target is located. One or more restricted zones (e.g., restricted zones 941-946) within the horticultural field may be identified, and the path may be revised to avoid any restricted zones within the horticultural field. In addition to restricted zones and macro-objects that can be determined through the observation of, for example, a wide-area field-of-view (FOV) camera or other device, the autonomous vehicles may be configured to detect and avoid smaller objects that may interfere with the movement of the vehicle. The vehicle may have an on-board real-time vision system that is capable of dynamic path planning around smaller objects, such as posts, wires, or humans that that were not previously detected. Additionally, such real-time vision systems can be used to aid the navigation of the vehicle and augment on-board guidance systems such as inertial navigation systems. After arriving at the local area, the autonomous vehicle may locate the target within the local area based on the identification of the target, and then subsequently perform the action with respect to the target.

The automated horticultural feedback process using such devices may be referred as an Autonomous Horticultural Feedback (AHF) process. An AHF system comprising various hardware and software components, as described in detail below, may be employed to perform an AHF process.

It should be noted while some of the examples described herein are illustrated in the context of ground robots, the described principles can be implemented with any type of autonomous moving or self-moving vehicle or device. The term "autonomous device" or "autonomous vehicle" may include any such vehicle or device and is used interchangeably herein. It should also be noted while some of the examples described herein are illustrated in the context of sensors and image capture devices, the described principles can be implemented with any type of data capture device, including RF sensors, audio sensors, particle capture and analysis devices (e.g., soil capture), and the like. The term "sensor" or "data capture device" may include any such device and is used interchangeably herein.

Additionally, the control of the autonomous vehicles may be centralized using one or more control systems that may be implemented on-premises or remotely, such as in the cloud. Additionally, the autonomous vehicles may form a decentralized mesh network that propagates data along each node. In this way, range of the AHF system may be indefinitely extended.

It should also be noted that various types of vehicles may be used to augment the techniques described herein. For example, a camera module and/or sensor payload, or any of the sensors described herein, can be attached to an agricultural vehicle to transmit data to the AHF system. Such vehicles can include but is not limited to seed drills, cultipackers, movers, farm trucks, tractors, plows, and manure spreaders. Any of these vehicles can be manned (manual) or autonomous. Additionally, a camera module and/or sensor payload can be attached to a non-agricultural vehicle, such as an all-terrain vehicle (ATV), automotive vehicle, non-motorized cart, and the like, to transmit data bak to the AHF system.

In some embodiments, sensors may be coupled to non-vehicles to augment the techniques described herein. For example, a camera module and/or sensor payload can be attached to a backpack, jacket, handheld module, hat, or any other apparatus that enables an individual to carry a payload to transmit data back to AHF system. All of the described methods can be used to supplement and enhance the data collection capabilities of the AHF system.

Horticultural data collected by an AHF system in an AHF process may include plant-related information as well as non-plant-related information. The plant-related information may include, but is not limited to, height of a plant, color of leaves, density of buds or flowers, size of fruits or grains, etc. The AHF system may facilitate collecting plant-related information via one or more autonomous devices instead of a human grower. For example, a ground robot may be equipped with one or more still image cameras or video cameras. The AHF system may maneuver the ground robot to a target plant within the horticultural field to capture pictures (i.e., still images) or a video of the target plant. The pictures or the video may be stored in a digital format, and subsequently analyzed by image processing algorithms to extract various plant-related information including the ones mentioned above. If equipped with multiple cameras, the ground robot may capture a binocular or multi-ocular image or video, which can indicate size of objects in the image or video.

The non-plant horticultural data collected by the AHF system may include contextual information that is not directly measured or gathered from a plant but is otherwise related to the growing environment of the plant. For example, the contextual information may include a temperature reading, a humidity reading, or an illumination reading of the ambient environment of a plant. The contextual information may also include an air pressure reading, or a pH level reading of the soil or water in which the plant is planted or immersed. The contextual information may also include data collected from CO2 sensors, and may include vapor (VPD). The contextual information may further include weather information, such as cloud cover, seasonality, or precipitation. Such data can be obtained from third party sources, or from weather stations at the growing operation itself. Similar to the collection of the plant-related information, the AHF system may also facilitate collecting contextual information via one or more robots instead of a human grower.

In some embodiments, an autonomous device such as a ground robot may be equipped with various sensors such as a thermometer, a hydrometer, a light meter, a barometer, an anemometer, and/or a pH meter. The AHF system may cause the ground robot to approach a target plant within the horticultural field, and collect contextual information such as ambient temperature, humidity, illumination, air pressure, wind speed, or pH level using the sensors equipped on the ground robot. In some embodiments, a video camera or a still image camera may be equipped on a ground robot, and the camera may be used to take video or pictures of plants or other non-plant objects in the horticultural field. Software algorithms, procedures, or programs may analyze the video or the pictures to extract contextual information around a target plant, such as an illumination condition, a weather condition, other horticultural activities being conducted, unexpected situations in the field/greenhouse, etc.

Alternatively, a ground robot may collect contextual information without being equipped with various sensors or cameras. That is, the various sensors described above may, instead of being disposed on a ground robot, be deployed in the horticultural field. The AHF system may maneuver a ground robot to a target plant, and the ground robot may communicate with the sensors deployed in a vicinity of the target plant to receive contextual information reported by the sensors. Some example methods for wireless communication to sensors include Bluetooth, NFC, LoRA, and RFID.

A further part of the AHF process may include one or more analysis functions that are configured to analyze the collected data and identify problems and issues based on the horticultural data that has been collected as described above. The process of obtaining horticultural knowledge and data over time from many multiple sources in the manner described can provide analysis and insights that may be difficult for a single farmer to arrive upon alone. The analysis functions may further determine possible causes of the problems, as well as a remedial course of action, such as making a diagnosis and determining a treatment plan based on various observed symptoms or conditions on. In some embodiments, the AHF system may still rely on an experienced human master grower to review the results of the analysis and identification of horticultural problems based on the horticultural data collected by the robots.

In some embodiments, the AHF system may incorporate computer-based machine learning capabilities or artificial intelligence (AI) to aid in the process of identifying a problem and a remedial solution based on the horticultural data collected from the field. The AHF system using this approach may facilitate a faster, more consistent, and more scalable AHF process. Such an AHF system may be referred as an Artificial Intelligence and Automated Horticultural Feedback (AIAHF) system. Compared with reliance on a human master grower, an AIAHF system may facilitate faster experience accumulation and more efficient learning, as the AIAHF system is able to cross-reference to horticultural feedback processes from a large number of grow operations, possibly across a wide range of geographic locations, whereas a human master grower is typically limited to a significantly fewer number of grow operations at one or a few locations.

In some embodiments, after an initial collection of horticultural data, the AHF system may decide to collect additional horticultural data before identifying a problem and/or prescribing a remedial solution. Namely, ground robots may be sent in several "waves" for collecting different kinds of horticultural data, or a same kind of horticultural data at different moments in time, before identifying a problem and/or prescribing a remedial solution.

The AHF system may also facilitate the execution or implementation of a remedial solution. For example, a remedial solution as determined may be communicated to human workers in the field, and the human field workers may operate certain horticultural tools, vehicles, or equipment, such as tractors, soil mixers, pruners, etc., to apply the remedial solution to target plants. In some embodiments, the AHF system may carry out a remedial solution using automatic or semi-automatic horticultural equipment. For example, the remedial solution may be increasing the water irrigation frequency from twice a day to four times a day. The remedial solution may be transmitted to a computer-controlled sprinkler system on the field and so applied to target plants. In some embodiments, the AHF system may carry out a remedial solution using robots in addition to human field workers. That is, robots may be utilized to perform a remedial solution. For example, the AHF system may determine that certain pesticide needs to be applied to a specific area of the horticultural field, and the AHF system may direct one or more ground robots to carry the pesticide to the specific area and apply the pesticide to the plants in the specific area.

A follow-up step may conclude the horticultural feedback process, wherein further monitoring of the plant after a remedial solution is applied may reveal whether the remedial solution has mitigated the problem successfully. The AHF system may facilitate an automation of this follow-up step by sending ground robots to collect horticultural data of a target plant after a remedial solution has been applied to the target plant. In some embodiments, the AHF system may send a ground robot to obtain a physical sample from a plant for further analysis.

Any part of the AHF process may be monitored by a master grower through one or more interfaces configured to provide access to the AHF system using various types of devices including mobile devices to enable continuous and as-needed communications. For example, a master grower may use a phone or desktop-based application to consume data. In some embodiments, an application programming interface (API) may be provided to facilitate the servicing of input and output to the AHF system.

The techniques pertinent to an AHF system enable the modern horticultural industry to manage grow operations in a scalable way, regardless of the size of the horticultural fields, the number of greenhouses, or whether the horticultural fields/greenhouses are at same or different geographic locations. Specifically, with the described techniques, the horticultural feedback process is no longer limited by the availability of experienced human master growers, a resource that is becoming more and more scarce and costly. As a grow operation scales up, the described techniques would ensure predictable crop yield and/or readiness with minimum increase in overhead cost.

The techniques described herein may be implemented in a number of ways. Example implementations are provided below with reference to the following figures.

FIG. 1 provides an example context diagram illustrating an AHF system 100 configured to perform AHF operations for a horticultural operation. A horticultural operation may include one or more outdoor open spaces that receive natural light (e.g., sunlight). Alternatively or additionally, the horticultural operation may include one or more indoor, enclosed spaces that receive natural light through windows and/or artificial light from a man-made light source (e.g., lamps). The horticultural operation shown in FIG. 1 includes an outdoor horticultural field F01 and an indoor greenhouse G02. Within the scope of present disclosure, the terms "horticultural field" and "greenhouse" may be used interchangeably when the context is irrelevant to the outdoor/indoor nature of a particular embodiment. Horticultural fields and/or greenhouses of a horticultural operation may be at geographic locations that are close to or away from each other. Each of the horticultural fields and the indoor greenhouses may cultivate one or more grow operations, such as grow operations 101 and 102 in field F01, as well as grow operation 103 in greenhouse G02. Each grow operation may grow a specific kind of plant or crop starting on a specific date. It's not necessary that all the growable space within a horticultural field or greenhouse be occupied by grow operations at any given time. For example, as shown in FIG. 1, field F01 still has some growable spaces that are not currently being used for growing plants or crops.

To collect horticultural data of a grow operation, AHF system 100 may employ a plurality of field sensors, such as sensors 111 deployed in field F01 or sensors 112 deployed in greenhouse G02. Sensors 111 and 112 may include, for example but not limited to, a thermometer for measuring an ambient temperature, a hydrometer for measuring an ambient humidity, a light meter for measuring an ambient illumination, a barometer for measuring an ambient air pressure, an anemometer for measuring an ambient wind speed, or a pH meter for measuring a pH level reading of the soil or water in which a plant is planted or immersed. Each of sensors 111 and 112 may be communicatively coupled to a local server physically located within a vicinity of field F01 or greenhouse G02. For example, local server 121 may be located in or close to field F01, and sensors 111 may be connected with local server 121 via wired or wireless communication links so that horticultural data of grow operations 101 and 102 may be collected by sensors 111 and subsequently transmitted to and stored in local server 121. Similarly, local server 122 may be located in or close to greenhouse G02, and sensors 112 may be connected with local server 122 via wired or wireless communication links so that horticultural data of grow operation 103 may be collected by sensors 112 and subsequently transmitted to and stored in local server 122. The horticultural data may be stored in local servers 121 and 122 with time stamps. That is, each entry of the horticultural data may denote which field sensor (i.e., which one sensor of sensors 111 or 112) the data entry was measured by, as well as a moment in time (i.e., a time stamp) at which the specific data entry was recorded by the specific sensor.

In some embodiments, power needed to operate sensors 111 and 112 may be supplied from a power supply by dedicated power wires. In some embodiments, power needed to operate sensors 111 and 112 may be supplied by solar panels, batteries, or other portable power sources disposed at respective locations of sensors 111 and 112.

In some embodiments, sensors deployed in a horticultural field may not transmit the horticultural data as collected to a local server via a direct communication link, be it a wired or wireless link. Rather, autonomous vehicles, such as ground robots, may be utilized to travel to a vicinity of a field sensor to collect horticultural data from the specific field sensor. That is, AHF system 100 may command one or more autonomous vehicles to travel to a plant of interest within the horticultural field, and subsequently collect horticultural data relevant to the plant of interest from one or more field sensors that are deployed in a vicinity of the specific plant.

In some scenarios, this approach of collecting horticultural data sensed by field sensors using robots and other autonomous devices may be preferred over direct communication links between field sensors and the local server. The scenarios may include a horticultural field that is relatively large in area and thus the infrastructure deployment of direct communication links between field sensors and the local server, whether wired or wireless, is relatively expensive or at least not economical. In some embodiments, a combination of both approaches of collecting horticultural data is possible. For example, for sensors that are physically located in a vicinity of a local server, direct communication links may be installed or otherwise established to couple those sensors to the local server. For sensors that are physically located rather far away from the local server, ground robots or other autonomous vehicles may be utilized to collect horticultural data as described above.

In some embodiments, AHF system 100 may assign missions to ground robots for performing certain steps of an AHF process, such as collecting horticultural data from field sensors. After being assigned a mission, a ground robot may maneuver to the horticultural field to execute the mission. In other embodiments, ground robots may perform missions without being directed by the AHF system 100 if conditions are sufficient to warrant a new mission.

When a ground robot is not executing a mission, the ground robot may be docked in a vehicle bay. In an example embodiment, a vehicle bay may be a structure in or near the horticultural field, able to host a plurality of ground robots therein. Each horticultural field may have one or more vehicle bays. As shown in FIG. 1, field F01 has two vehicle bays 141, and greenhouse G02 has one vehicle bay 142. Each of vehicle bays 141 and 142 may host or otherwise accommodate one or more ground robots of ground robots 131 or ground robots 132 when the one or more ground robots are not deployed.

In some embodiments, a vehicle bay may serve as a power station to ground robots. Namely, a vehicle bay may be equipped to provide power or fuel to the ground robots, UAVs, or other devices docked therein. Ground robots 131 and 132 and UAVs 133 of AHF system 100 may be powered by electricity, fuel, or a hybrid of both electricity and fuel. Some of the ground robots 131 and 132 and UAVs 133 may be equipped with a hybrid engine to convert fuel to electricity. When docked in a vehicle bay of vehicle bays 141 and 142, a ground robot of ground robots 131 or ground robots 132 or UAVs 133 may have its fuel tank replenished, or battery recharged, via the vehicle bay. In some embodiments, a vehicle bay may serve as a data transfer station for a ground robot docked therein. Namely, a vehicle bay may be equipped with a storage device, and various data may be transferred from the ground robot to the storage device, or vice versa, when the ground robot is docked inside the vehicle bay. Moreover, a vehicle bay may exchange data with a ground robot via a wireless means, especially when the ground robot or UAV is within a wireless communication range from the vehicle bay. The storage device may be communicatively coupled to a local server. For example, one or both of vehicle bays 141 may be equipped with a respective storage device, which may be communicatively coupled to local server 121. Similarly, vehicle bay 142 may be equipped with a storage device, and the storage device may be communicatively coupled to local server 122. In general, a vehicle bay may serve as a power station, a data transfer station, or both. In some embodiments, AHF system 100 may also include a vehicle bay that serves neither as a power station nor as a data transfer station. Instead, the specific vehicle bay may only serve as a parking station, providing ground robots or UAVs a safe place to park in the horticultural field between executing missions. A vehicle bay may be provided with an enclosing device such as a door, a cover, or a ceiling. The enclosing device may close to shield ground robots or UAVs docked in the vehicle bay from weather or other external disturbance. When a ground robot or UAV needs to enter or leave the vehicle bay, the enclosing device may open to provide a passage for a docked ground robot to go airborne or for an airborne ground robot to dock. Additionally, vehicle bay 142 may itself form a mesh network. In some embodiments, a mesh network of bays can be used to extend range indefinitely, which can serve UAVs or UGVs in their vicinity.

For embodiments where AHF system 100 does not include direct communication links between field sensors 111 and local server 121, or between field sensors 112 and local server 122, missions may be assigned to ground robots 131 and 132 and UAVs 133 to collect horticultural data from one or more sensors of field sensors 111 and 112. For example, field sensors 112 of greenhouse G02 may operate upon opto-electrical power sources, without being communicatively coupled to local server 122 via direct communication links. AHF system 100 may thus utilize ground robots and UAVs to collect horticultural data from field sensors 112. A mission may dictate a ground robot of ground robots 131 and 132 and UAVs 133 to travel to a vicinity of one or more sensors of field sensors 112 deployed in greenhouse G02. The mission may further dictate the ground robot or UAV to collect horticultural data, with time stamps, from the one or more sensors of field sensors 112 using various wireless communication techniques between the sensors and the ground robot, such as Wi-Fi, Bluetooth, Zigbee, infrared, or other low-power/short-range wireless communication technologies. The horticultural data may temporarily be stored in an on-board memory the ground robot is equipped with. As the ground robot or UAV approaches one of vehicle bay 142, or docked therein, the horticultural data may be uploaded or otherwise transmitted to a storage device provided at vehicle bay 142. The horticultural data may be further uploaded to local server 122 via a communication link between the storage device of vehicle bay 142 and local server 122.

In addition to field sensors 111 and 112, AHF system 100 may employ a plurality of cameras, such as still image cameras and/or video cameras, to collect horticultural data. For example, cameras 151 may be strategically placed in field F01 to monitor grow operations 101 and 102 of field F01. Cameras 151 may take still images or video recordings of a specific area of grow operations 101 and 102 as horticultural data for AHF system 100. Likewise, cameras 152 may be strategically placed in greenhouse G02 to monitor grow operation 103. Cameras 152 may take still images or video recordings of a specific area of grow operation 103 as horticultural data for AHF system 100.

Cameras 151 and 152 may be communicatively coupled to local servers 121 and 122, respectively, so that the still images and/or video recordings may correspondingly be uploaded to local servers 121 and 122. In some embodiments, cameras 151 and 152 may have low light or night vision capabilities for monitoring field F01 and greenhouse G02 during dawn and dusk hours, at night, or under a low illumination condition. The still images and video recordings captured by cameras 151 and 152 may be used or otherwise analyzed to provide horticultural data such as an estimate height, an estimated density of flower buds or fruits, an estimated size or quantity of produces, etc., regarding a grow operation or a specific plant thereof.

In some embodiments, AHF system 100 may include ground robots or UAVs that are equipped with various cameras and sensors. Horticultural data may thus be sensed or otherwise captured directly by the onboard cameras and sensors of the ground robots or UAVs as the ground robots traverse the horticultural field to different grow operations thereof. Strictly speaking, the use of sensing to obtain horticultural data by onboard cameras and sensors of ground robots, which may be referred as an "onboard-sensing" approach, may be exclusively employed by AHF system 100 without resorting to the "field-sensing" approach described earlier, i.e., sensing to obtain horticultural data by field sensors 111 and 112 as described above. Nevertheless, "onboard sensing" and "field sensing" can be mutually complimentary and may both be employed by AHF system 100 to work in concert with one another.

In order for AHF system 100 to be capable of performing onboard sensing, one or more of ground robots 131 and 132 and UAVs 133 may be equipped with at least a camera (e.g., a still image camera or a video camera) or a sensor (e.g., a thermometer, a hydrometer, a light meter, a barometer, an anemometer, or a pH meter). The camera may be used to capture a picture or a video of a grow operation as plant-related horticultural data, whereas sensors may be used to collect contextual information of a grow operation as non-plant-related horticultural data. Regarding the use of an onboard camera, AHF system 100 may assign a mission, for instance, to a ground robot 131 equipped with a camera to perform the mission. The mission may contain an identification (e.g., a QR code, a serial number, an identification number, or a bar code) of a target plant within field F01, as well as an action to be performed with respect to the target plant. For example, the mission may instruct the ground robot 131 to travel to a target plant of grow operation 102 to capture pictures or a video recording of the target plant. The still images or the video recording may temporarily be stored in an onboard memory of the ground robot 131 while the ground robot 131 is still deployed in the field, and subsequently uploaded to local server 121 that is communicatively coupled to a vehicle bay 141 after the ground robot 131 is docked in the vehicle bay 141. For some missions, the onboard camera may be able to provide certain horticultural data without actually recording or otherwise storing a picture or a video recording. For instance, the ground robot may monitor a grow operation with the camera turned on, and an estimated height of the plants in the grow operation may therefore be estimated by the camera. Regarding using onboard sensors, AHF system 100 may assign a mission, for instance, to a UAV 133 equipped with a light meter to perform the mission. The mission may contain an identification of a target plant within greenhouse G02, as well as an action to be performed with respect to the target plant. For example, the mission may instruct UAV 133 equipped with a light meter to travel to a target plant of grow operation 103 to measure an illumination reading in a vicinity of the target plant. The illumination reading may temporarily be stored in an onboard memory of the UAV 133 as the UAV 133 is still deployed, and subsequently uploaded to local server 122 that is communicatively coupled to vehicle bay 142 after the UAV 133 is docked in vehicle bay 142. Alternatively, the illumination reading may be readily transmitted, via a wireless means, to a storage device of vehicle bay 142 while the UAV 133 is still deployed. In some embodiments, the illumination reading may be transmitted directly to local server 122 before the UAV 133 is docked in a vehicle bay such as vehicle bay 142.

In some embodiments, horticultural data may include a physical sample of a plant. A ground robot may be equipped with a robotic arm capable of taking a physical sample of a plant, such as a few leaves, some grains, or a fruit, of the plant. The ground robot may also be equipped with a sample container for storing the sample. After a physical sample is acquired from the plant (e.g., a specific plant of grow operation 101) by the robotic arm and placed in the sample container, the ground robot may transport the physical sample to a master grower onsite (e.g., master grower 195 who is working in field F01) so that the master grower may examine the physical sample. In some embodiments, a ground robot may be equipped with a sample container, but without a robotic arm capable of taking a physical sample of a plant. The sample may instead be acquired by a worker in the field (e.g., field worker 191). The field worker may carry a handheld communication device (e.g., personal communication device 193), via which the field worker may be informed of what physical sample is to be acquired from which plant.

With an exception of a physical sample, horticultural data, after being collected from field F01 or greenhouse G02, may be stored in local server 121 or 122, respectively, and subsequently be utilized by AHF system 100 in the AHF process. For example, the horticultural data may be examined or otherwise analyzed by a human master grower, such as master grower 198, to identify various horticultural problems pertinent to the grow operations. As shown in FIG. 1, master grower 198 may not be onsite. That is, master grower 198 may be located remotely from field F01 and greenhouse G02, and horticultural data that has been uploaded and stored in local servers 121 and 122 may be accessed by master grower 198 remotely. Master grower 198 may access the horticultural data via data communication network 196. In some embodiments, horticultural data stored in local servers 121 and 122 may be transmitted to central server 199 via network 196 for further processing or analysis.

Data communication network 196 may comprise a local area network (LAN), a wide area network (WAN), a mobile network, an Internet, or a combination of two or more thereof. The horticultural data may be presented to master grower 198 via a user device 197. The user device 197 may be a laptop computer, smartphone, desktop computer, tablet, or any other computing device. The user device 197 can be connected to local systems or cloud-based systems.

In some embodiments, the user device 197 may be used to define the boundaries of local areas/fields by placing markers on a map. In one example, a grower may open and execute a mobile application and submit a request to register a new growing area or operation. The grower may use the mobile application to place marker on a map, defining the boundaries of the growing area as an n-sided polygon, or some regular shape such as a circle, square, etc. By using the user device 197 to define the boundaries, the need for manually placing boundary markers around fields/growing areas may be eliminated, thus making the described techniques more scalable. The identification of local areas/fields can also be automated using machine learning, thereby reducing or eliminating the need for the master grower to define boundaries. Additionally, when a grower is using a mobile phone/tablet to traverse the growing operation, the mobile application may automatically determine the identification of in-proximity fields. For example, the grower may approach a field in a large area of land. The mobile application can provide an indication that the grower is approaching an identified field so that the grower can know which specific field is being approached. This can provide useful guidance during the planting process.

In some embodiments, at least part of the horticultural data stored in local server 121 or 122 may be rendered or otherwise processed by functions that implement one or more algorithms before being presented to master grower 198. For example, grow operation 101 of field F01 may be growing cabbage. Horticultural data pertinent to grow operation 101, as stored in local server 121, may include pictures of grow operation 101. An image processing algorithm may process the pictures and render the pictures to indicate by highlights some cabbage plants of grow operation 101 that may be showing yellowish leaves. Master grower 198 may access the pictures with the highlights and identify a potential horticultural problem pertinent to the cabbage plants having yellowish leaves. As another example, grow operation 103 of greenhouse G02 may be growing roses, which may be in a growing phase of producing flower buds. Horticultural data pertinent to grow operation 103, as stored in local server 122, may include a first video recording of grow operation 103 recorded on a first date, as well as a second video recording of grow operation 103 recorded on a second date that may be a few days after the first date. An image processing algorithm may compare the first and second video recordings and indicate with indications in the video recordings some rose plants of grow operation 103 that may be producing significantly fewer flower buds as compared to other rose plants of grow operation 103. Master grower 198 may access the video recordings having the indications and identify a potential horticultural problem pertinent to the rose plants producing fewer flower buds.

In either example above, master grower 198 may not need to access and examine all "raw data", i.e., horticultural data as obtained and stored in local server 121 or 122, which may have been a time-consuming task, not to mention network 196 would have been heavily loaded and become inefficient. Instead, the software algorithms, through processing the raw data, help to direct the attention of master grower 198 to those plants that may have a higher probability of having a horticultural problem. Due to the scarcity of horticultural experts available, master grower 198 could have been a bottleneck of a horticultural feedback process in a traditional approach. The bottleneck may be relieved in AHF system 100 thanks to the employment of the software algorithms processing raw horticultural data. Certain computation power of a computer may be needed for running or otherwise executing the software algorithms on the computer. In some embodiments, local server 121 or 122 may be taking the computation burden. That is, the software algorithms may be running on local server 121 or 122, where the raw horticultural data is readily available. In some embodiments, AHF system 100 may shift the computation burden to a central server 199, which may be more powerful than local servers 121 or 122 in terms of running the software algorithms more efficiently. That is, central server 199 may access the raw horticultural data stored in local servers 121 and 122, process the raw horticultural data by running the software algorithms, and save the processing result in central server 199. Master grower 198 may thus examine the processing result on user device 197 by accessing the processing result stored in in central server 199 via network 196. In some embodiments, central server 199 may duplicate the raw horticultural data stored in local servers 121 and 122. The duplicated copy may be saved in a storage device of central server 199 as a backup copy, in case the original copy of the raw horticultural data stored in local server 121 or 122 is somehow lost, deleted, or damaged.

Based on the horticultural data, be it raw or software rendered, master grower 198 may identify various horticultural problems that need to be addressed in field F01 and/or greenhouse G02. Furthermore, master grower 198 may prescribe or otherwise determine a remedial solution (i.e., a remedial course of action) to address or mitigate the horticultural problems. For example, based on the horticultural data stored in local server 121 and pertinent to grow operation 102 of field F01, master grower 198 may identify that specific cabbage plants of grow operation 102 may have yellowish leaves, indicating a horticultural problem of the cabbage plants, as the yellowish leaves may be an indication of the cabbage plants not being healthy. Master grower 198 may determine that the cabbage plants need more water irrigation to address this horticultural problem. Master grower 198 may assign to local server 121, via network 196, a remedial solution which, upon being executed, may address the horticultural problem. Specifically, the remedial solution may be an extra twenty minutes of irrigation per day for the cabbage plants for a week. Local server 121 may command a robot deployed in field F01, such as irrigation robot 161, to carry out the remedial solution. Irrigation robot 161 may locate in field F01 the cabbage plants that need more water, and then irrigate them according to the remedial solution prescribed by master grower 198. As another example, based on the horticultural data stored in local server 122 and pertinent to grow operation 103 of greenhouse G02, master grower 198 may identify that specific rose plants of grow operation 103 may be producing fewer number of rose buds than expected, a horticultural problem of the rose plants. Master grower 198 may determine that the rose plants need to receive more illumination to address this horticultural problem. Master grower 198 may assign to local server 122, via network 196, a remedial solution which, upon being executed, may address the horticultural problem. Specifically, the remedial solution may be an additional four hours of illumination per day for the rose plants. Local server 122 may command an illumination device deployed in greenhouse G02, such as illumination device 162, to carry out the remedial solution. Illumination device 162 may locate in greenhouse G02 the rose plants that need more illumination, and then provide them with additional illumination according to the remedial solution prescribed by master grower 198. In an event that illumination device 162 is not configured to be controlled directly by local server 122, a field worker 192 may operate illumination device 162 manually to provide the additional illumination. Local server 122 may wirelessly transmit the remedial solution to a personal communication device 194 carried by field worker 192 so that field worker 192 may be informed about the remedial solution. Alternatively, personal communication device 194 may be connected with network 196. Master grower 198 may prescribe the remedial solution via user device 197, and the remedial solution may be transmitted to personal communication device 194 via network 196 so that field worker 192 may be informed about the remedial solution.

In various embodiments, AHF system 100 may have horticultural data examined or analyzed, horticultural problems identified, and corresponding remedial solutions determined, all without a human master grower, e.g., master grower 198. Central server 199 may, for example, be include AI functions configured to analyze horticultural data, identify horticultural problems, and determine corresponding remedial solutions. Horticultural data stored in local servers 121 and 122 may be transmitted to central server 199 to be analyzed by the AI functions of central server 199. In some embodiments, the AI functions of central server 199 may work in concert with master grower 198. For example, the AI functions may deal with routine horticultural problems, whereas human master grower 198 may deal with horticultural problems that are more advanced, complicated, or uncommon.

Additionally or alternatively, AI functions may be built into a local server, such as local servers 121 and 122. AI functions in a local server may provide analysis, diagnosis, and remedial solutions in a way that is more specific to the respective horticultural field, because the AI functions have been trained using horticultural data collected from the horticultural field. The use of local servers can also reduce network overhead, for example due to downloading of neural networks or other machine learning models. In some embodiments, training may be performed off-site or in the cloud. Data incorporated from different growing operations can be used to increase the performance of artificial intelligence (AI) models.

After a remedial solution is applied as prescribed, AHF system 100 may conclude the AHF process by further monitoring the plants that have been treated according to the remedial solution, so that an effectiveness of the remedial solution may be assessed. Similar to the collection of horticultural data before a horticultural problem is identified, horticultural data of plants after the remedial solution has been applied to the plants may be collected from field F01 or greenhouse G02 using one or more of ground robots 131 or 132, possibly in conjunction with field sensors 111 or 112, as described above.

FIG. 1 also illustrates cloud-based resources 180 that is connected to network 196. Some or all of the functionality described above with regard to FIG. 1 may be implemented in the cloud-based resources 180. In some embodiments, cloud-based resources 180 may provide computing and storage resources on-demand and as needed. In other embodiments, most or all of the storage and computing functions may be performed using cloud-based resources 180. In this case, local server 121, 122 and central server 199 may not be utilized. In some embodiments, functionality may be distributed between cloud-based resources 180 and on-site resources.

When traversing a horticultural field to perform various AHF missions, a ground robot is required to position itself within the horticultural field so that the ground robot may navigate while traversing the horticultural field. In some embodiments, the positioning/navigation function may be realized by a global positioning system (GPS) receiver disposed on the ground robot. For example, each of ground robots 131 and 132 may be equipped with such a GPS receiver. The GPS receiver of the robot may receive positioning signals from a plurality of space-based satellites. The GPS receiver may further triangulate the positioning signals to determine a three-dimensional (3-D) geophysical position of the robot on the Earth surface.

The effectiveness of a GPS receiver may be compromised if the reception of the satellite-originated positioning signals is less than ideal. The quality of reception of the positioning signals may be affected by weather, electromagnetic interference/shielding, or physical blocking. For example, whereas a ground robot 131 serving the open field F01 may receive satellite signals most of the time, a ground robot 132 serving the enclosed greenhouse G02 may at times experience difficulties determining its position using GPS, as the building structure of greenhouse G02 may block or at least greatly attenuate the GPS satellite signals. Therefore, positioning mechanisms other than using a GPS, such as the positioning mechanism illustrated in FIG. 2, may be provided to an AHF system such as AHF system 100.

Figure 2:
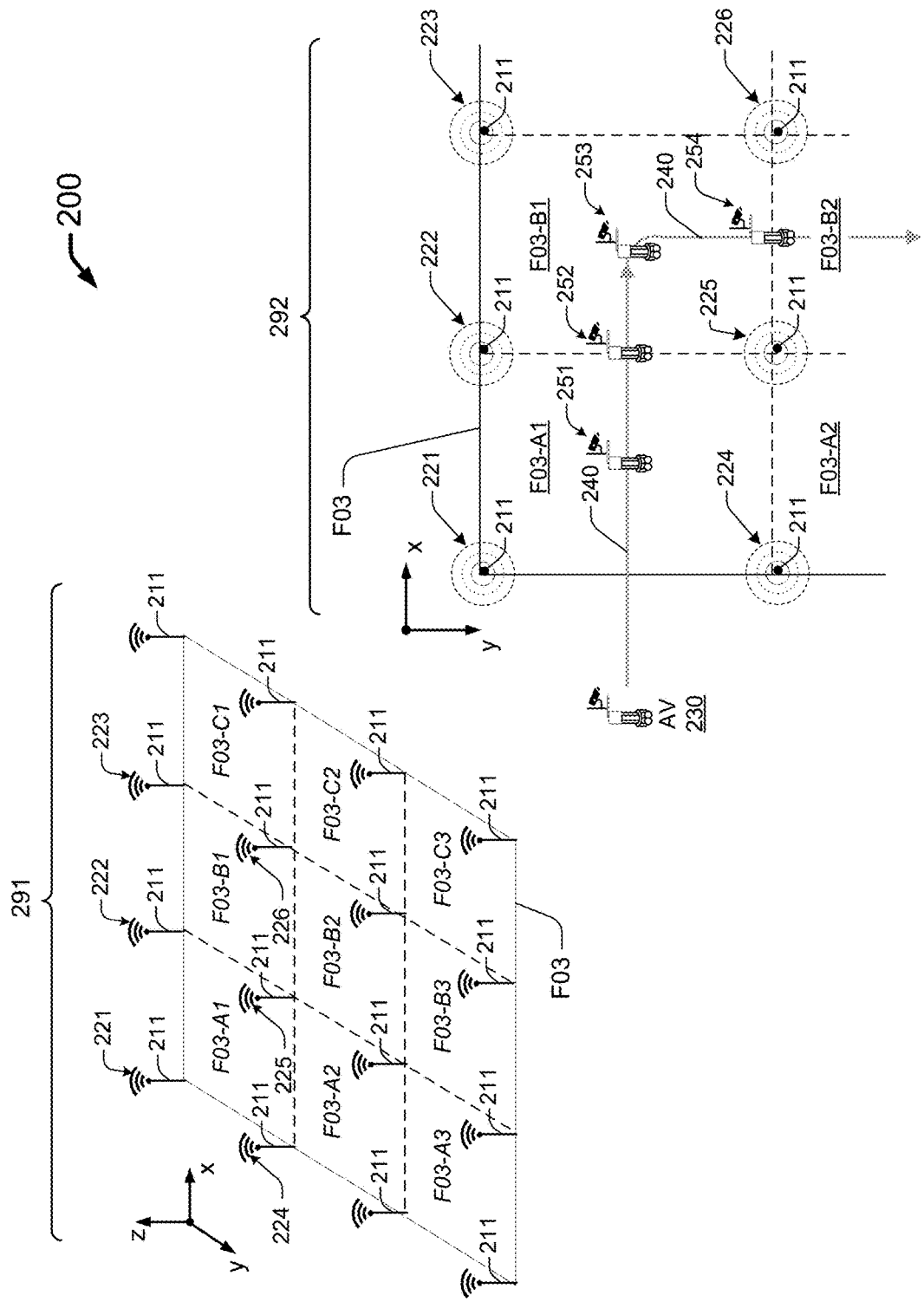
FIG. 2 illustrates a positioning mechanism applicable to an AHF system.

FIG. 2 illustrates an example positioning mechanism 200 that is applicable to AHF system 100 in an implementation with ground robots. For the purpose of positioning a robot within a horticultural field, the horticultural field is often divided into a plurality of local areas, which are smaller in size. In general, a horticultural field may be divided into local areas that are similar in respective size, and the local areas may collectively form a matrix. In some embodiments, however, a horticultural field may be divided into local areas of various sizes, especially if the shape of the horticultural field is irregular. A horticultural field may be divided into local areas using radio beacons disposed in the horticultural field. The beacons emit radio signals that enable a ground robot receiving the signals to determine its location relative to the beacons. Beacon signals can, for example, uniquely identify their source beacon, indicate location (e.g., coordinates) of the beacon emitting them, indicate a direction to the beacon emitting them, indicate a degree or standard of power, and so forth.

As shown in FIG. 2, horticultural field F03 is divided into nine local areas that collectively form a 3×3 matrix. View 291 illustrates a 3-D perspective view of field F03, whereas view 299 illustrates a top view of a portion of field F03. A plurality of beacons 211 may be disposed across field F03 to define the local areas of field F03. The local areas of field F03 are referred in FIG. 2 as F03-A1, F03-A2, F03-A3, F03-B1, F03-B2, F03-B3, F03-C1, F03-C2, and F03-C3, respectively. Although each of beacons 211 may be physically identical, each of the plurality of beacons 211 may emit a respective beacon signal, i.e., a self-identifying radio signal. Refer to local area F03-A1 of FIG. 2, which is largely of a rectangular shape, as an example. A respective beacon 211 is disposed at each of the four corners of local area F03-A1, and is emitting a beacon signal. As shown in both view 291 and view 299, the four beacons disposed at the corners of local area F03-A1 are emitting beacon signals 221, 222, 224 and 225, respectively. Also shown in view 291 and view 299 are two other beacon signals 223 and 226, which are being emitted from the two beacons 211 that are disposed at the two corners of local area F03-B1 that are not neighboring local area F03-A1. Beacon signals 221-226 may be encoded in respectively unique radio patterns so that they are self-identifying. When a beacon signal emitted from a specific beacon 211 is received by an antenna, the radio pattern embedded in the beacon signal may uniquely reveal which beacon 211 the beacon signal is emitted from.

The self-identifying radio signals emitted from beacons 211, such as beacon signals 221-226, may be utilized by a ground robot 230 (depicted in the figure as an autonomous vehicle or "AV") to identify the location of ground robot 230 within field F03 as ground robot 230 traverses field F03. Ground robot 230 may use various radio-based trilateration techniques for positioning. In some embodiments, the self-identifying radio signals, including beacon signals 221-226, may be emitted from beacons 211 with a constant signal strength. That is, each of the beacon signals may exhibit the same signal strength at the transmitting end, i.e., at a respective beacon 211. Since signal strength of a radio signal continues to decay as the radio signal travels further away from its origin, ground robot 230 may translate the strengths of the beacon signals, as received by ground robot 230 at its immediate position, into corresponding distances between ground robot 230 and beacons 211, at least in relative terms. The position of ground robot 230 within field F03 may accordingly be determined or otherwise inferred based on the distances by interpolation or extrapolation. For example, ground robot 230 may be traversing field F03 along a path 240 while constantly receiving radio signals 221-226 emitted from beacons 211. Let S231 denote the signal strength of beacon signal 221 as received by ground robot 230 at an immediate position of ground robot 230. Also let S222, S223, S224, S225 and S226 denote the signal strengths of beacon signals 222, 223, 224, 225 and 226 as received by ground robot 230 at its immediate position, respectively. In response to a condition where S221, S222, S224 and S225 are substantially the same, ground robot 230 may infer that its immediate location is at or around location 251 within field F03, i.e., around a center location of local area F03-A1. In response to a condition where S222, S223, S225 and S226 are substantially the same, ground robot 230 may infer that its immediate location is at or around location 253 within field F03, i.e., around a center location of local area F03-B1. In response to a condition where S221, S223, S224 and S226 are substantially the same, ground robot 230 may infer that its immediate location is at or around location 252 within field F03, i.e., around a center location of a contiguous area formed by local areas F03-A1 and F03-B1.

In addition to positioning, the beacon signals emitted by beacons 211 may also be utilized for navigation. For example, ground robot 230 may be currently at location 253, and S222, S223, S225 and S226 are substantially the same. In order to continue moving along path 240 toward location 254, ground robot 230 may move incrementally toward a direction so that S225 and S226 increases at a same rate while S222 and S223 decreases at a same rate.

In some embodiments, ground robot 230 may position or navigate without beacon signals of a constant signal strength being emitted by beacons 211. Specifically, beacons 211 may emit beacon signals in a synchronized manner, wherein the beacon signals are not required to have a same signal strength when leaving beacons 211. ground robot 230 may position and navigate within field F03 not based on signal strengths of the beacon signals as received, but based on propagation delays of the beacon signals. A propagation delay of a beacon signal is defined by the time the beacon signal takes to arrive at the immediate location of ground robot 230 after being sent from a respective beacon 211.

Since the division of a horticultural field into local areas is based on the radio signals of beacons, the boundaries of the local areas are imaginary, and may not stay fixed from an administration point of view. Based on specific horticultural needs, the number and boundaries of local areas of a horticultural field may be changed, usually between horticultural seasons. The beacons may be re-arranged, with or without an increase or decrease in a total number of beacons, to divide a horticultural field into local areas in a different way as compared to a previous horticultural season. In some embodiments, QR codes that are visible from the UAV/UGV may also be used.

An AHF system may include an administrative scheme, which is a plan for maintaining a database comprising various information items that collectively reflect a status of one or more horticultural fields administrated by the AHF system. Each of FIGS. 3-8 and 10-12 illustrates an information item of the administrative scheme, as described below in detail. The administrative scheme marshals, in a real-time and/or just-in-time manner, various status or information of a horticultural field during an AHF process performed by the AHF system. Specifically, for each horticultural field administrated by the AHF system, the administrative scheme may facilitate real-time or just-in-time marshaling of information regarding AHF activities. The real-time/just-in-time information may include but is not limited to: (1) names of plant, locations, and growing phases of various grow operations currently growing in the horticultural field; (2) respective locations of individual plants within a grow operation; (3) zones within the horticultural field in which ground robots are operable or non-operable; (4) status of ground robots servicing the horticultural field; and (5) status of past AHF missions, current AHF missions, and planned AHF missions.

FIG. 3 shows an example operation dashboard 300 as an information item of the administrative scheme of AHF system 100. According to operation dashboard 300, AHF system 100 is currently administrating four horticultural fields: F01, G02, F03, and F04. Each of the four horticultural fields is growing one or more grow operations, and each grow operation is uniquely identified by an operation ID in operation dashboard 300. For example, horticultural field F04 is growing four different grow operations: op120, op222, op512, and op664. Operation dashboard 300 also records, for each grow operation, the name of the crop or plant that is growing, as well as a respective growing phase of the crop or plant at the moment. For instance, operation dashboard 300 records that operation op512 is a grow operation growing yellow corn, and is currently in growing phase 1. Operation dashboard 300 also shows that operation op222 has cabbage in growing phase 4. The "growing phase 1" information regarding operation op512 may indicate that the corn plants of operation op512 were planted just recently, whereas the "growing phase 4" information regarding operation op222 may indicate that the cabbage plants of operation op222 are almost ready to be harvested. More information regarding each grow operation may be included in operation dashboard 300, such as a start date and an estimated harvest date of the grow operation, an acreage of the grow operation, various horticultural substances (e.g., fertilizer, pesticide) that have been applied to the grow operation, and so forth.

Figure 4:
FIG. 4 illustrates a local area map of a horticultural field.

The administrative scheme of AHF system 100 may include a local area map for each horticultural field, as each horticultural field may be divided into a plurality of local areas using beacons or QR codes, as exemplified in FIG. 2. The local area map may specify a unique identifier for each of the local areas of the horticultural field. FIG. 4 illustrates a local area map 400 of field F04, as another information item of the administrative scheme of AHF system 100. As shown on local area map 400, field F04 is divided as a 7×7 matrix having forty-nine local areas, each identified with a respective identifier. For example, the seven local areas in the first column of the matrix are specified with identifiers A1, A2, A3, A4, A5, A6, and A7, respectively, wherein the seven local areas in the middle row of the matrix are specified with identifiers A4, B4, C4, D4, E4, F4, and G4, respectively.

The administrative scheme of AHF system 100 may include a physical structure map for each horticultural field. The physical structure map may illustrate or otherwise record locations of various physical structures or objects in the horticultural field. AHF system 100 may refer to the physical structure map for various administrative purposes. For example, AHF system 100 may refer to the physical structure map when moving grow operations within the horticultural field, or when assigning horticultural missions to ground robots. Publicly available 3D data can be used to define the structure map in order to help automate this process.

Figure 5:
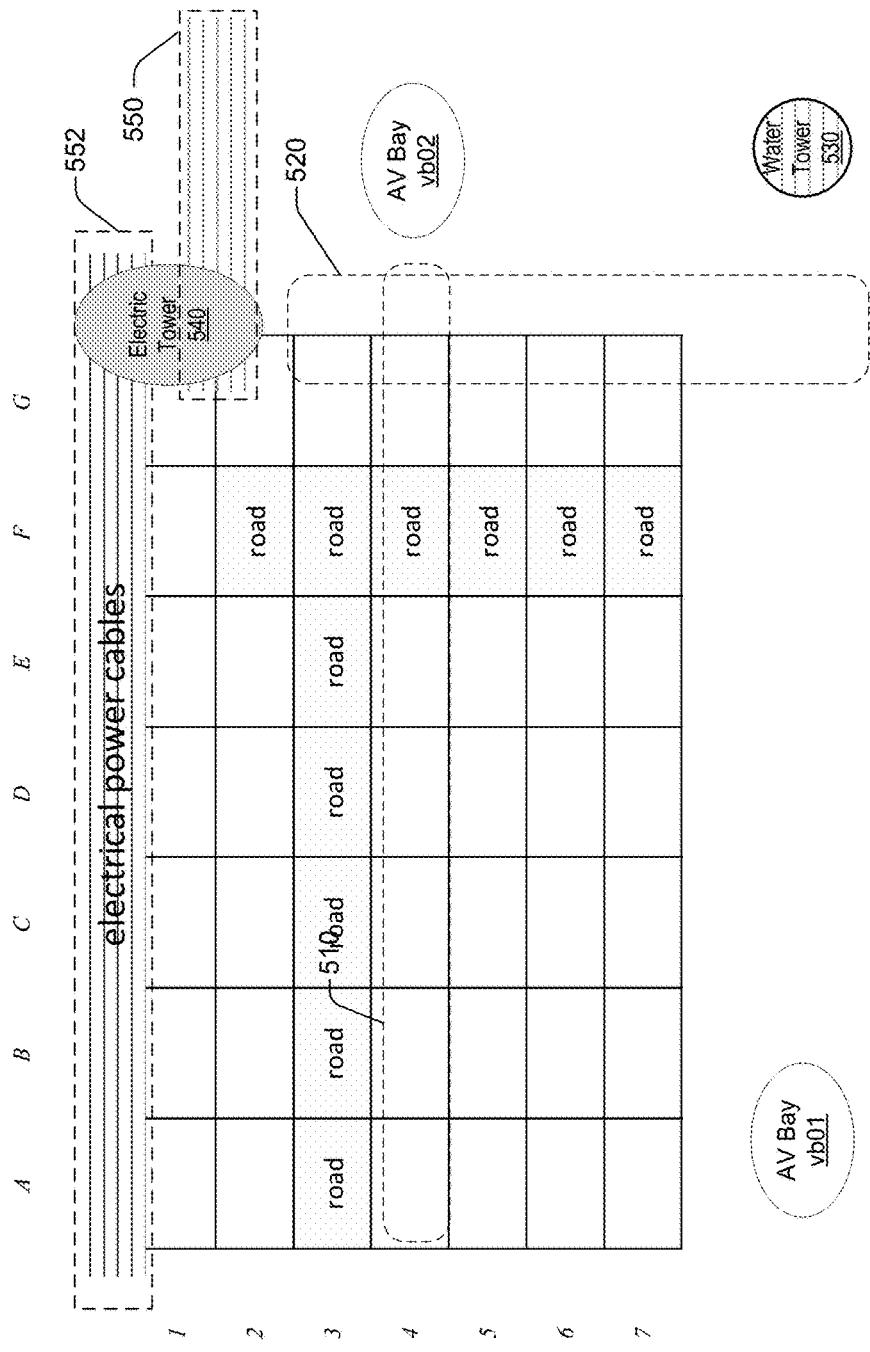
FIG. 5 illustrates a physical structure map of a horticultural field.

FIG. 5 illustrates a physical structure map 500 of field F04, as another information item of the administrative scheme of AHF system 100. As shown on physical structure map 500 and with reference to local area map 400, field F04 has a road 510 extending from local area A3 to local area F3, as well as a road 520 extending from local area F3 to local area F7. The roads 510 and 520 may be used for ground traffic of horticultural vehicles (e.g., trailer, tractors, or trucks), and may not be used as part of a grow operation. Additionally, physical structure map 500 also shows that field F04 has a water tower 530 in local area G7, an electric tower 540 in local area F1, and two ground robot bays (i.e., vehicle bays for ground robot) vb01 and vb02 located in local area A7 and local area G3, respectively. Local areas occupied by the various physical structures (e.g., roads 510 and 520, water tower 530, electric tower 540, ground robot bays vb01 and vb02) may not be available as part of a grow operation, at least not completely available. Some physical structures, however, may permit land usage for growing plants. For example, electrical power cables in an area 550 may pass through the local area G1 in the air, but would still allow local area G1 to be used as part of a grow operation.

An area 552 that is occupied by electrical power towers and cables is also specified on physical structure map 500. Even though area 552 is not officially within the boundaries of field F04, the proximity of the electrical power cables in area 552 may interfere or otherwise affect certain horticultural activities performed within field F04. For example, to avoid interference with electrical power cables in the area 552, ground robots traversing across field F04 near the area 550 (especially over local areas A1, B1, C1, D1, E1) can maneuver in zones safely avoiding the electrical towers and power cables.

Figure 6:
FIG. 6 illustrates a grow operation map of a horticultural field.

The administrative scheme of AHF system 100 may include a grow operation map for each horticultural field. The grow operation map may show or otherwise indicate which local areas of a horticultural field are being occupied by which grow operations. FIG. 6 illustrates a grow operation map 600 of field F04, as another information item of the administrative scheme of AHF system 100. As shown on grow operation map 600, grow operation op120 is taking up local areas A5-A7 and B5-B7; grow operation op222 is taking up local areas D5-D7, E5 and E6; grow operation op512 is taking up local areas A1, A2, B1 and B2; grow operation op664 is taking up local areas G1, G2 and G4-G6. Combining grow operation map 600 and operation dashboard 300, a utilization of Field 04 may be comprehensively presented. In some embodiments, information contained in grow operation map 600 may be integrated into operation dashboard 300.

The administrative scheme of AHF system 100 may include a field activity map for each horticultural field. The field activity map may show or otherwise indicate various horticultural activities scheduled to happen within a span of time, for instance, one day. Some of the horticultural activities may direct to a grow operation currently growing in the horticultural field. Some of the horticultural activities may be directed to a grow operation that has not started growing, or a grow operation that has recently been harvested. FIG. 7 illustrates a field activity map 700 of field F04 for the day of May 22$^{nd}$, as another information item of the administrative scheme of AHF system 100. As shown on field activity map 700, on May 22$^{nd}$, soil plowing activities will be conducted in local areas C1 and C2 of Field F04. Additionally, harvesting will be conducted in local areas D5-D7, and post-harvest clean-up activities will be conducted in local areas E5 and E6.

When a ground robot traverses a horticultural field, it is imperative that the ground robot avoids certain restricted zones (RZs) and obstructions identified by the administrative scheme. In general, an RZ may include a portion of a local area bounded by a geometric shape such as a rectangle. An RZ may also include portions of several local areas wherein the portions are continuous. Ground robots would want to avoid the RZs to ensure safety and regulation observance. Ground robots may refrain from entering RZs so that they do not run into various physical structures on the horticultural field. Additionally, the RZ may include identification of local areas that include specific obstructions that may be identified, for example, using geographic coordinates or other means for identifying a location.

Ground robots may refrain from entering RZs so that they may not interfere with horticultural activities that may obstruct ground robot movement. Ground robots may refrain from moving through certain areas to avoid interfering with the plants of the grow operation, wherein the RZ may be determined based on an estimated perimeter of the canopy of the plants of the grow operation, plus some safety or clearance margin. Space reserved for ground traffic, or around an area reserved for foot traffic, may be identified as an RZ. Depending on the weather (e.g., wind gust, lightning, hail), certain areas of the horticultural field may be adversely affected, and those areas may be identified as RZs. In addition, government regulations may forbid operation of ground robots in certain areas, and those areas may also be identified as RZs by the administrative scheme of the AHF system.

FIG. 8 illustrates an RZ map 800 of field F04 for the day of May 22$^{nd}$, as another information item of the administrative scheme of AHF system 100. As shown on RZ map 800, restrictions, if any, are specified for each local area of field F04. For example, the administrative scheme of AHF system 100 may limit ground robots entering a local area reserved for ground traffic so that ground robots may not interfere with tractors or other ground vehicles that may be in the ground traffic. Therefore, RZ map 800 may specify that local area F1 is an RZ.

Likewise, other physical obstructions on or near field F04 may dictate some RZs on RZ map 800. For example, an obstruction may be identified in local area C3, and another physical obstruction may be identified in local area F5. In determining a path for a ground robot, RZs on RZ map 800 are to be observed and avoided.

Figure 9:
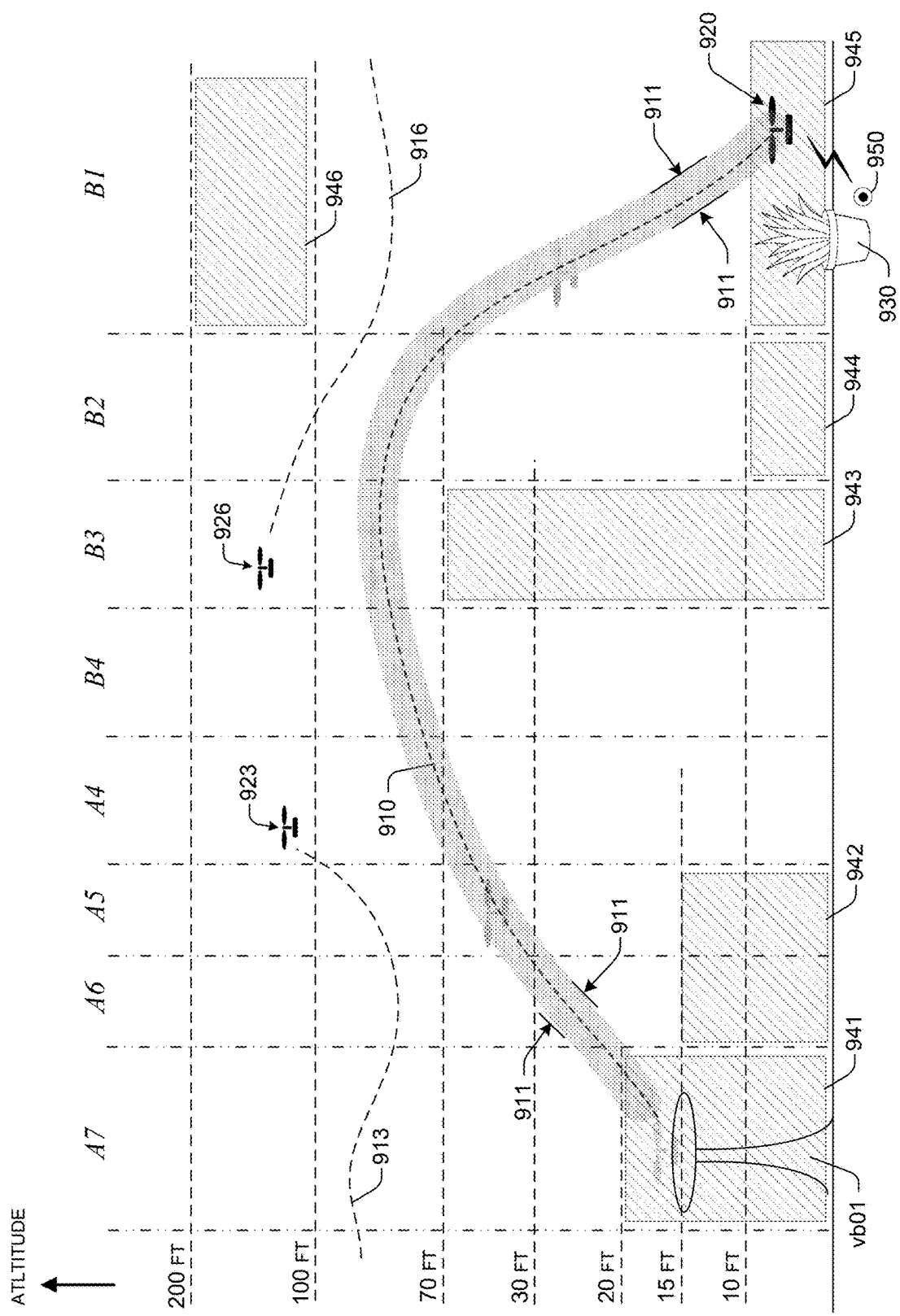
FIG. 9 illustrates example paths for autonomous vehicles utilized by an AHF system.

FIG. 9 illustrates an example path using the example of unmanned aerial vehicles (UAVs). FIG. 9 illustrate an example path 910 for a UAV 920, as determined by RAHF system 100, after UAV 920 is assigned a horticultural mission to collect certain horticultural data regarding a target plant 930 of field F04. The mission may comprise collecting a pH level reading of the soil that grows target plant 930. When the mission is assigned, UAV 920 may be docked in UAV bay vb01, which is located in local area A7 according to physical structure map 500. The target plant 930 may be located in local area B1 of field F04. Also shown in FIG. 9 are NFZs 941, 942, 943, 944, 945 and 946, which are consistent with the altitude limits specified in NFZ map 800. Specifically, path 910 avoids NFZs 941-946. It shall be noted that path 910's avoiding NFZs 941-946 does not mean path 910 is completely exclusive from NFZs 941-946 in all the local areas path 910 intersects with. In fact, path 910 may enter an NFZ in a local area where it starts, and path 910 may enter an NFZ in a local area where it ends. However, path 910 does not intersect with an NFZ when traveling through local areas in between. Traveling along path 910, UAV 920 may originate from UAV bay vb01 in local area A7, pass sequentially through local areas A6, A5, A4, B4, B3, B2 along path 910, and arrive at target plant 930 in local area B1. Since the height of UAV bay vb01 is typically below the flying altitude limit set by an NFZ, it is obvious that UAV 920 would be in NFZ 941 when leaving UAV bay vb01. Also, for UAV 920 to collect the pH level reading from pH meter 950 embedded in the soil growing target plant 930, it is obvious that UAV 920 has to be within a wireless communication range from pH meter 950, which may require UAV 920 to enter NFZ 945 when in local area B1. Nevertheless, UAV 920 does not enter any of the NFZs 941-946 when passing through local areas A6, A5, A4, B4, B3, and B2. For paths that neither originate nor end in local area A7, such as path 913 for UAV 923, NFZ 941 has to be observed and avoided. Likewise, for paths that neither originate nor end in local area B1, such as path 916 for UAV 926, NFZ 945 has to be observed and avoided.

When UAV 920 travels "along" path 910, UAV 920 may not be moving exactly "on" path 910 during the whole time of the traveling. Rather, when UAV 920 travels along path 910, UAV 920 may be located close to path 910 within a range of proximity 911. The range of proximity 911 may be dependent, at least partly, on how well UAV 920 may position and navigate itself. External aviation factors, such as sidewind or local air vortex, may also affect the range of proximity 911.

An RZ map of a horticultural field, such as RZ map 800, may be updated constantly to reflect, in a real-time or just-in-time manner, RZ changes due to weather change or weather forecast, crop growth, or horticultural activities happening in the horticultural field. For example, on May 20$^{th}$, cabbage plants of grow operation op222 are not yet harvested, and the May 20$^{th}$ RZ map of field F04 may indicate that ground robots are free to travel in local areas D5, D6, D7, E5, and E6. Namely, RZs in local areas D5, D6, D7, E5, and E6 include only space at 15 ft altitude or below. On May 21$^{st}$, cabbage plants in local areas E5 and E6 are being harvested, and the May 21$^{st}$ RZ map may expand RZs in local areas E5 and E6 to accommodate the harvest activity. According to field activity map 700, cabbage plants in local areas D5-D7 are to be harvested on May 22$^{nd}$. Therefore, RZ map 800, of May 22$^{nd}$, indicates that RZs in local areas D5-D7 are also added. Meanwhile, RZ map 800 indicates that RZs in local areas E5 and E6 are added as the horticultural activity in local areas E5 and E6 on May 22$^{nd}$ would be post-harvest cleaning according to field activity map 700. Likewise, even though local areas C1 and C2 are not currently growing a grow operation, an RZ may be indicated on RZ map 800 for the two local areas. The RZ in local areas C1 and C2 is identified so that ground robots may not interfere with a horticultural activity of soil plowing, which is indicated on field activity map 700.

The update rate of RZ map 800 may be as frequent as every minute or more often, so that RZ map 800 is essentially true in a real-time sense. The most recent version of RZ map 800 may be sent to every ground robot in service, especially to those that are deployed for missions, so that the ground robots may avoid all RZs on RZ map 800, including the most recently updated ones, when traversing field F04. In some embodiments, information regarding the RZs of RZ map 800 may be saved into an RZ list, which may be transmitted to every ground robot in service. The RZ list may essentially include the same information as represented by RZ map 800. Each ground robot in service may store a copy of the RZ list onboard for reference by a navigation module of the respective ground robot. As RZ map 800 gets changed, the associated RZ list may be updated accordingly and transmitted to ground robots. A ground robot may accordingly change or otherwise update its planned path to conform to the updated RZ list.

In some embodiments, an update to an RZ map may be triggered by cameras deployed in the horticultural field. For example, an RZ map regarding field F01 of FIG. 1 may be triggered by any of cameras 151, and an RZ map regarding greenhouse G02 of FIG. 1 may be trigger by any of cameras 152. Cameras 151 and 152 may observe various horticultural activities, planned and unplanned, in field F01 and greenhouse G02, and trigger an RZ update should an activity may interfere with ground robot operation. For example, a camera 151 may observe that irrigation robot 161 has been deployed unexpectedly (e.g., not as planned according to a field activity map of field F01), which may impede ground robot movement in certain local areas. The RZ map may be updated such that the affected space is included in the RZs. Ground robots servicing field F01 may receive an updated RZ list, and adjust respective travel paths to avoid the local areas affected by the unexpected operation of irrigation robot 161. In some embodiments, autonomous vehicles with on-board vision may be able to avoid smaller obstacles such as deployed robots. The generation of the RZ can just be adjusted based on the capabilities of the autonomous vehicles.

Likewise, field sensors may also trigger an RZ update. For example, anemometers deployed in field F04 may sense a wind gust at 20:00 of May $22^{nd}$, and AHF system 100 may determine that the wind gust is too strong for ground robots av02, av03, av04 and av08 to operate safely in certain local areas of field F04. AHF system 100 may update RZ map 800 accordingly, at least for ground robots av02, av03, av04 and av08, which may each receive an updated RZ list. Each of ground robots av03, av04 and av08, while deployed, may change its respective travel path based on the updated RZ list. In some embodiments, a field sensor may trigger a temporary hold of all the ground robot operations for a horticultural field. For example, field sensors 112 deployed in greenhouse G02 may include an earthquake detector. Upon the earthquake detector sensing an earthquake of a significant scale, AHF system 100 may determine to immobilize all ground robots servicing greenhouse G02 until the earthquake subsides. AHF system 100 may cause the ground robots to immobilize by updating an RZ map of greenhouse G02 to include all local areas of greenhouse G02. Alternatively, AHF system 100 may directly issue an emergency immobilization command to cause all deployed ground robots in greenhouse G02 to suspend all movement immediately, instead of updating the RZ map and sending updated RZ lists to ground robots.

In some embodiments, not all ground robots in service may share the same RZ list. Namely, a ground robot servicing field F04 may have an RZ map 800 containing RZ information tailored to the specific ground robot, whereas another ground robot servicing field F04 may have a different RZ map 800 containing different RZs. For example, ground robots may have differences in speed and maneuvering capabilities, safety margins, or other specifications. For example, a zone having certain terrain characteristics may be traversed based on the ground robot capabilities, whereas the terrain may represent a safety concern to other ground robots.

The administrative scheme may also facilitate a centralized dashboard showing status of robots, including ground robots, being used in the AHF system. FIG. 10 shows an example ground robot dashboard 1000, which is another information item of the administrative scheme of AHF system 100. ground robot dashboard 1000 reflects status of ground robots that service field F04, as of 20:00 on May $22^{nd}$. Similar to RZ map 800, ground robot dashboard 1000 may be frequently updated to provide a real-time/just-in-time effectiveness of the status. ground robot dashboard 1000 includes status of ten ground robots, av01-av10. For each ground robot thereof, ground robot dashboard 1000 records a current status in general, an immediate location, a mission ID representing a horticultural mission that has been assigned to the respective ground robot, a fuel or battery level, whether the respective ground robot is available for a new mission assignment, various resources the respective vehicle is equipped with (e.g., sensors, cameras, memory, sample containers, etc.), and other specifications (e.g., payload). As shown in ground robot dashboard 1000, three out of the ten ground robots, i.e., av03, av07 and av08 have been assigned a mission that is either being or yet to be executed. In some embodiments, a ground robot having an assigned mission may not be assigned another mission until the currently assigned mission has been completed or canceled. In some embodiments, a ground robot may be assigned multiple missions, wherein the missions are enqueued for the ground robot to execute in sequence.

As shown in ground robot dashboard 1000, five out of the ten ground robots listed in ground robot dashboard 1000 are currently unavailable for a new mission assignment for various reasons. ground robot av03 is unavailable because it is currently deployed and has a mission assignment, mission m10080. Ground robot av05 is unavailable due to a mechanical problem of the ground robot. ground robot av07, although already docked in ground robot bay vb01, is unavailable because it is transferring horticultural data from mission m10073 that it just executed to a storage device of ground robot bay vb01. ground robot av06 is unavailable because its battery charge level is too low. To prevent a ground robot from running out of fuel or battery power in the middle of executing a horticultural mission, AHF system 100 may impose a power threshold for the ground robots, which requires a ground robot to dock and replenish fuel or charge a battery to a level above the power threshold before the ground robot becomes available for a new mission. In some embodiments, the power threshold may be a range of values, so as to provide a hysteresis function in ground robot power management. For example, AHF system 100 may impose a power threshold of 10%-40%. That is, a ground robot is forced to dock and replenish fuel or charge a battery when the power level of the ground robot drops below 10%, and the ground robot is not available to receive a new mission assignment until the ground robot regains its power level over 40%. As shown in ground robot dashboard 1000, ground robots av06 and av09 are respectively docked in a vehicle bay and charging. Ground robot av09 is available for mission assignment because its current battery charge level, at 45%, is already higher than the power threshold (i.e., 10%-40%). In contrast, ground robot av06 is not yet available for mission assignment because its current battery charge level, which is at 20%, is still not higher than the minimum departure power threshold of 40%. In some embodiments, AHF system 100 may impose a memory threshold on the ground robots in a concept similar to a power threshold. As described above, each ground robot may be equipped with an onboard memory device for temporarily storing horticultural data (e.g., pictures of a target plant or video of a grow operation). Therefore, the memory threshold is imposed to prevent ground robots from running out of onboard memory for storing horticultural data during a horticultural mission, very much in a similar way the power threshold is imposed to prevent ground robots from running out of power during a horticultural mission. For example, AHF system 100 may impose a memory threshold of two gigabytes (GB) of free or available memory. That is, a ground robot may not be assigned a new mission unless the ground robot has at least 2 GB of free memory. Accordingly, ground robot av10 is unavailable for a mission because its onboard memory is too full, having only 0.3 GB left, which is less than the memory threshold (i.e., 2 GB of free memory). ground robot av10 may need to free up some of the onboard memory so that it may have more than 2 GB of free memory, before ground robot av10 may become available to take on a new mission. ground robot av10 may do so by uploading some of the horticultural data currently stored in the onboard memory to a storage device of a vehicle bay, or directly to a local server, through either wired or wireless means.

On the other hand, the other five ground robots listed in ground robot dashboard 1000 (i.e., ground robots av01, av02, av04, av08 and av09) are immediately available for a new mission assignment. Ground robots av01, av02 and av09 are docked in vehicle bay vb01. Ground robot av04 may have just finished another mission and is still flying, currently in local area G6. Although airborne, ground robot av04 is also available for a new mission. ground robot av08, in some embodiments, may not be available for taking on a new assignment, as it may still be transmitting horticultural data collected from mission m10077 while traveling in local area D6. In some embodiments, however, ground robot av08, may be allowed to accept a new mission assignment, especially if the new mission involves a target plant that is in or around local area E6. The horticultural data from mission m10077 may still be continuously uploaded until the upload is complete while ground robot av08 executes the new mission.

The administrative scheme may also facilitate a centralized dashboard showing status of horticultural missions of the AHF system. FIG. 11 shows an example mission dashboard 1100, which is another information item of the administrative scheme of AHF system 100. Mission dashboard 1100 reflects status of horticultural missions having been, being, or yet to be performed by ground robots in field F04, as of 20:00 on May 22$^{nd}$. Similar to RZ map 800 and ground robot dashboard 1000, mission dashboard 1100 may be frequently updated to provide a real-time/just-in-time effectiveness of the status of the missions. Six example missions are listed in mission dashboard 1100, each identified with a unique mission ID, i.e., m10061, m10070, m10073, m10077, m10080, and m10091. Each mission includes a target located within field F04, as well as an action to be performed with respect to the target. For some missions (e.g., m10061 and m10070), the target may be a grow operation in its entirety. For some missions (e.g., m10073, m10077 and m10091), the target may be one or more local areas within a grow operation. For some missions (e.g., m10080), the target may be one or more specific plants within a local area. Mission dashboard 1100 also records, for each mission, the action to be performed with respect to the target. In mission dashboard 1100, each mission may have a respective mission status recorded as one of the following: "to be assigned", "assigned", "in progress", or "completed". A mission having a "to be assigned" status is a mission that has been entered or otherwise initiated into AHF system 100, but has yet to be assigned to a ground robot. A mission having an "assigned" status is a mission that has been assigned to a ground robot, but the execution of the mission by the ground robot has not yet started. A mission having an "in progress" status is a mission the execution of which has been started. A mission having a "completed" status is a mission that has been completed. Among the missions listed in mission dashboard 1100, missions m10061 and m10070 have been completed, missions m10073, m10077 and m10080 are being executed, whereas mission m10091 has not been assigned to a ground robot.

Each horticultural mission in mission dashboard 1100 is respectively recorded with an "entry time" and an "intended time window". The entry time of a mission is the time the mission is entered or otherwise initiated in AHF system 100. A mission may be entered or initiated by master grower 198, or the AI functions of central server 199. A mission for collecting horticultural data may be pre-scheduled to monitor growing conditions of grow operations. A mission for implementing a remediation solution may be entered upon a possible horticultural issue is identified based on the horticultural data collected. The intended time window of a mission, which may be designated by master grower 198 or the AI functions of central server 199 when the mission is entered, is a period of time during which the mission is intended to carry out. For example, according to mission dashboard 1100, mission m10061 was entered at 13:00 on May 22$^{nd}$, and was intended to be executed between 15:00 and 17:00 on the same day.

In addition, mission dashboard 1100 also record which ground robot(s) each mission is assigned to. For example, mission m10061 was assigned to, and has been executed by, ground robot av01, whereas mission m10073 is assigned to, and being executed by, ground robot av07. In some embodiments, a mission may not be assigned to a ground robot soon after the mission is entered. In fact, it may be preferred not to assign a mission until a short time before the intended time window of the mission. In some cases, a mission may even be assigned during the intended time window, as long as the mission can be completed within the intended time window. For example, mission m10073 is entered at 13:30 on May 22$^{nd}$ but not intended to be executed until some time between 17:00 and 19:00 on the same day. Accordingly, AHF system 100 may not assign mission m10073 to a ground robot until a short time (e.g., 5 to 10 minutes) before 17:00. Alternatively, AHF system 100 may not assign mission m10073 to a ground robot until after 17:00. By making short the time difference between mission assignment and the intended time window of the mission, the utilization of ground robots may be more efficient. For instance, this approach may make it more likely that the mission be assigned to a most suitable ground robot at the time the mission is intended to carry out. It may also avoid a situation where a ground robot is tied up to a future mission and thus unavailable to a more immediate mission.

As stated above, a target of a mission may be a specific plant of a grow operation. The specific plant may be identified in an AHF system using a unique identification. For example, mission m10080 in mission dashboard 1100 is intended for a target having an identification "pu_1231", which may represent a unique plant in field F04. Specifically, mission m10080 intends to collect a measurement reading of the pH level of the soil in which the unique plant represented by identification "pu_1231" is planted. To this end, the administrative scheme of AHF system 100 may include a plurality of plant unit (PU) lists, which make up another information item of the administrative scheme of AHF system 100. Each PU list corresponds to a specific local area of a specific horticultural field, and records which PUs are contained in the local area. Therefore, by searching through the PU lists, AHF system 100 is able to determine within which local area of which field a specific PU is located.

In some embodiments, PUs may be individual planters (e.g., containers that hold soil and plants), and each planter may grow a plant or several plants. In some embodiments, PUs may not be physical planters, but simply imaginary designations of plants for administrative purposes. For example, plants in a local area may be growing in rows or clusters but not in physical planters, and each cluster or row of plants may be designated as a PU of the local area. Each PU is uniquely identified by a PU identification (hereinafter referred as a "PUID") within AHF system 100. Namely, a PU is uniquely identified by its PUID among all the PUs of all the horticultural fields managed by AHF system 100.

Figure 12:
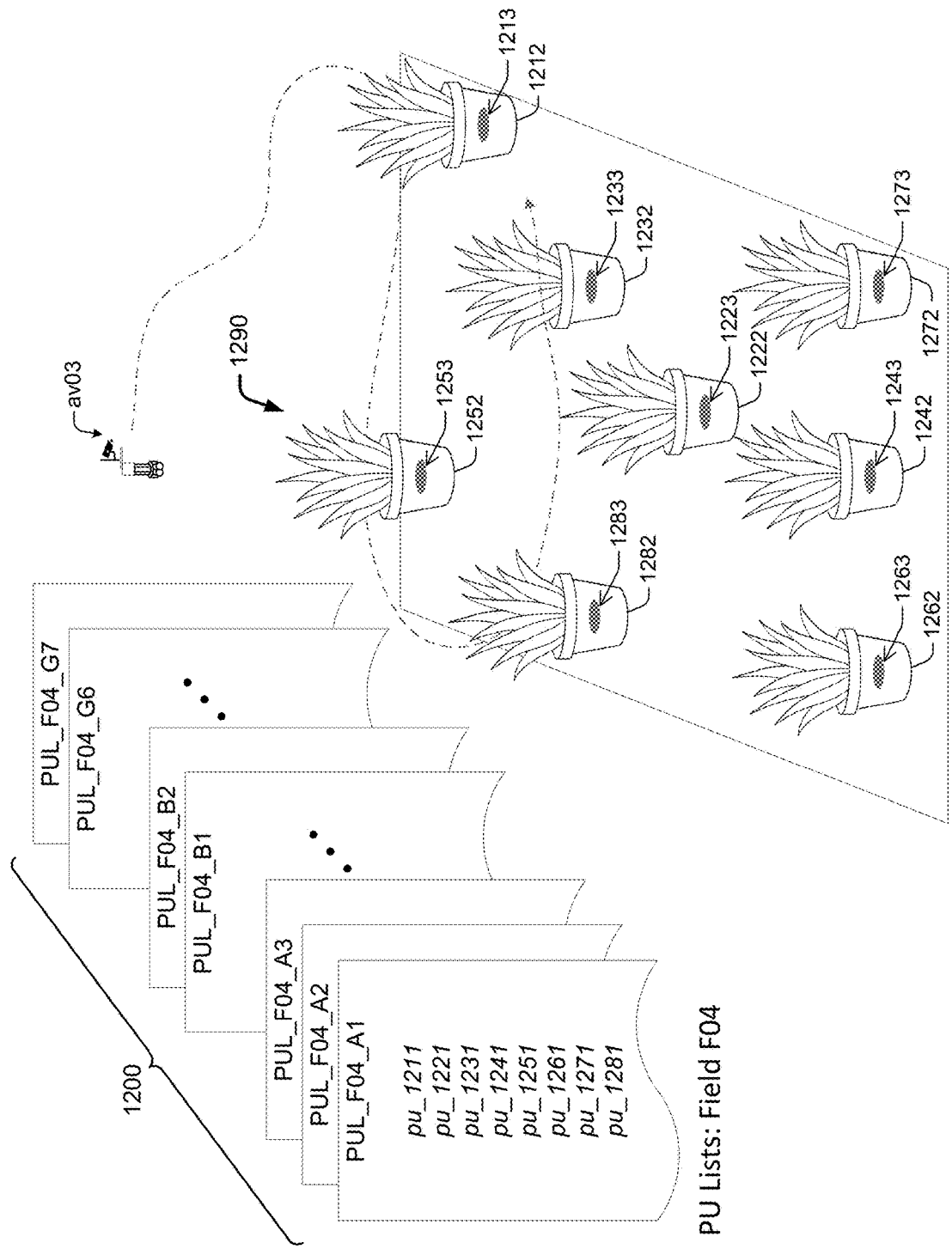
FIG. 12 illustrates plant unit lists of a horticultural field as well as plant units in a corresponding local area of the horticultural field.

FIG. 12 illustrates a plurality of PU lists 1200 of field F04. Each of PU lists 1200 corresponds to a local area of field F04. As shown in local area map 400, field F04 has a total number of forty-nine local areas, i.e., local areas A1, A2, A3, . . . , G5, G6, G7. Therefore, PU lists 1200 may include a total number of forty-nine lists, each respectively corresponding to one of the local areas of field F04. Specifically, PU lists 1200 includes a PU list for local area A1, and the PU list, labeled as "PUL_F04_A1" in FIG. 12, records eight PUIDs, i.e., pu_1211, pu_1221, pu_1231, pu_1241, pu_1251, pu_1261, pu_1271 and pu_1281. Each of the eight PUIDs may uniquely represent a PU in local area A1 of field F04. As shown in still image picture 1290 of local area A1 of field F04, local area A1 includes a total number of eight PUs, i.e., PUs 1212, 1222, 1232, 1242, 1252, 1262, 1272 and 1282. Each of the eight PUs is identified by one of the eight PUIDs recorded in PU list PUL_F04_A1. Moreover, each of the eight PUs may be provided with one of PU labels 1213, 1223, 1233, 1243, 1253, 1263, 1273 and 1283. Each of the PU labels may read or otherwise reveal the respective PUID of the PU to which the PU label is provided. A PU label may be placed at a known location on or around a PU (e.g., on the sidewall of a planter, or on a stick next to the PU). In some embodiments, a PU label may be a visual marker containing one or more visual codes, such as a barcode or a QR code. In some embodiments, especially for horticultural missions in low light conditions, a PU label may be a radio frequency identification (RFID) label. In either way, a PU label provided at a PU is able to reveal the PUID of the PU when recognized by a camera or scanned by a radio frequency (RF) scanner. When a ground robot approaches the plants in local area A1 of field F04, the ground robot may use a visual camera or a RF scanner equipped in the ground robot to scan the PU labels and identify the plants in the PUs. Specifically, upon the scanning, PU label 1213 attached to PU 1212 may reveal PUID pu_1211, which uniquely identifies PU 1212 in AHF system 100. Likewise, PU label 1223 attached to PU 1222 may reveal PUID pu_1221 upon the scanning. PU label 1233 attached to PU 1232 may reveal PUID pu_1231 upon the scanning. PU label 1243 attached to PU 1242 may reveal PUID pu_1241 upon the scanning. PU label 1253 attached to PU 1252 may reveal PUID pu_1251 upon the scanning. PU label 1263 attached to PU 1262 may reveal PUID pu_1261 upon the scanning. PU label 1273 attached to PU 1272 may reveal PUID pu_1271 upon the scanning. PU label 1283 attached to PU 1282 may reveal PUID pu_1281 upon the scanning. It should be understood that the partitioning of an area into a grid is provided as an example, and that the partitioning of a field/local area into any shape may be implemented.

With the aid of the PU lists of the administrative scheme and the PU labels physically disposed in the field, a specific plant in a horticultural field may be located. For example, according to mission dashboard 1100, mission m10080 requires locating a target identified by PUID pu_1231. Searching through PU lists 1200, AHF system 100 may find that the target is located in local area A1 of field F04. A ground robot, such as ground robot av03, may travel to local area A1 of field F04. After arriving at local area A1, ground robot av03 may scan some or all of the PU labels 1213, 1223, 1233, 1243, 1253, 1263, 1273 and 1283 by maneuvering near PUs 1212, 1222, 1232, 1242, 1252, 1262, 1272 and 1282 in a systematic way (e.g., moving from row to row, or moving from the edges of local area A1 spirally toward the middle of local area A1, etc.). Ground robot av03 may continue the maneuvering and the scanning until a PU label reveals PUID pu_1231. For instance, ground robot av03 may start from the first row of the PUs and maneuver to a vicinity of PU 1212 and scan PU label 1213, which reveals PUID pu_1211, different from the target PUID pu_1231. Ground robot av03 may subsequently maneuver to a vicinity of PU 1252 and scan PU label 1253, which reveals PUID pu_1251, also different from the target PUID pu_1231. Ground robot av03 may subsequently move to the second row of the PUs and maneuver to a vicinity of PU 1282 and scan PU label 1283, which reveals PUID pu_1281, also different from the target PUID pu_1231. Ground robot av03 may subsequently maneuver to a vicinity of PU 1232 and scan PU label 1233, which reveals PUID pu_1231, matching the target PUID. In this way, ground robot av03 is able to locate PU 1232, located in local area A1 of field F04, as the target of mission m10080.

As described above, for horticultural field F04, the administrative scheme of AHF system 100 may include the following set of administrative items: operation dashboard 300, local area map 400, physical structure map 500, grow operation map 600, field activity map 700, RZ map 800, ground robot dashboard 1000, mission dashboard 1100, and PU lists 1200. Each of the administrative items may be updated constantly in a real-time or just-in-time manner. Since the administrative information residing in the administrative items is pertinent to field F04, it can be advantageous to store the set of administrative items in a local server that is physically located within a vicinity of field F04. For each horticultural field serviced by AHF system 100, the administrative scheme may include a similar set of administrative items (i.e., an operation dashboard, a local area map, a physical structure map, a grow operation map, a field activity map, an RZ map, a ground robot dashboard, a mission dashboard, and a plurality of PU lists) pertinent to the respective horticultural field, and the set of administrative items may be stored in a local server of the horticultural field. For example, the administrative scheme of AHF system 100 may include a set of administrative items pertinent to field F01, and the set of administrative items may be saved in local server 121. Likewise, the administrative scheme of AHF system 100 may also include a set of administrative items pertinent to greenhouse G02, and the set of administrative items may be saved in local server 122. Central server 199 and master grower 198 may access, edit, and update the administrative items for any horticultural field of AHF system 100 via network 196 and user device 197. Additionally, field worker 191 may access, edit, and update the administrative items of field F01 stored in local server 121 via personal communication device 193. Likewise, field worker 192 may access, edit, and update the administrative items of greenhouse G02 stored in local server 122 via personal communication device 194.

In some embodiments, central server 199 may keep a synchronized copy of the administrative items of each horticultural field. This approach may enable central server 199 to marshal administrative information across various horticultural fields, from which AHF system 100 may benefit. For example, ground robot dashboard 1000 indicates that ground robot av05, capable of lifting a heavy weight, is having a mechanical problem and thus not available for a horticultural mission. Central server 199 may thus command another ground robot capable of a high payload to move from adjacent field F03 to filed F04 for a horticultural mission that requires a high payload ground robot.

Figure 13:
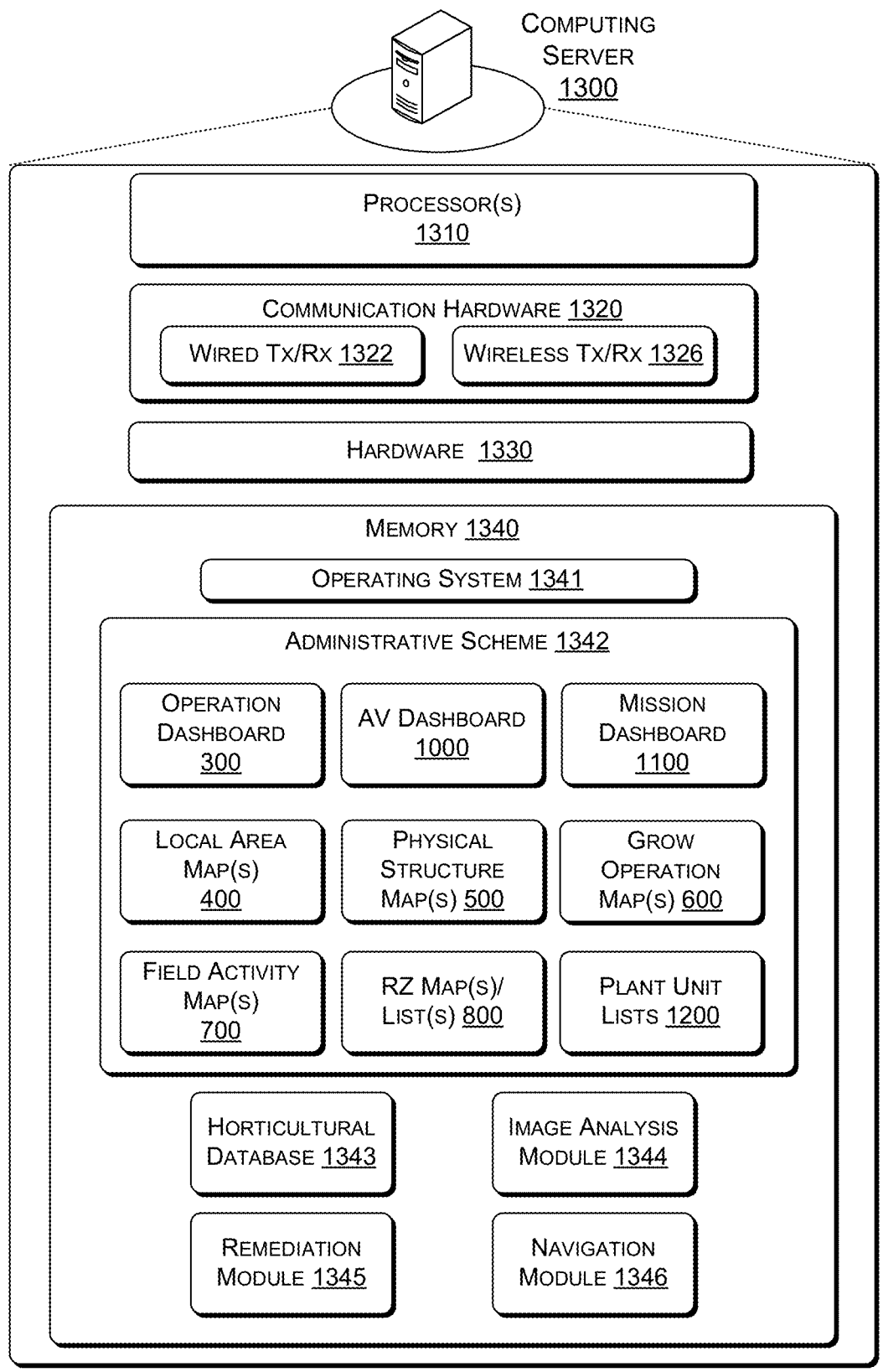
FIG. 13 is a block diagram showing various components of a computing server of an AHF system.

FIG. 13 illustrates a block diagram of a computing server 1300, which may embody a local server (e.g., local server 121 or 122) or a central server (e.g., central server 199) of AHF system 100. As shown in FIG. 13, computing server 1300 may include one or more processors 1310, a communication hardware 1320, hardware 1330, and memory 1340.

Communication hardware 1320 may include a wired transceiver 1322 for wired communications, and a wireless transceiver 1326 for wireless communications. Communication hardware 1320 may enable computing server 1300 to communicate with other devices of AHF system 100, such as field sensors (e.g., sensors 111 and 112), robots (e.g., ground robots 131 and 132, irrigation robot 161), horticultural devices (e.g., illumination device 162), ground robot bays (e.g., vehicle bays 141 and 142), field-deployed visual devices (e.g., cameras 151 and 152), personal communication devices (e.g., personal communication devices 193 and 194), and network 196. Various horticultural data and administrative information may be transmitted and/or received through communication hardware 1320.

Hardware 1330 may include other hardware that is typically located in a computer or server. For example, hardware 1330 may include signal converters, transceivers, antennas, hardware decoders and encoders, graphic processors, and/or the like that enable computing server 1300 to execute applications or software programs, procedures, or algorithms.

Memory 1340 may be implemented using non-transitory computer-readable media, such as computer storage media. Computer-readable media includes, at least, two types of computer-readable media, namely, computer storage media and communications media. Computer storage media includes volatile and non-volatile, removable and non-removable media implemented in any method or technology for storage of information such as computer-readable instructions, data structures, program modules, or other data. Computer storage media includes RAM, ROM, EEPROM, flash memory or other memory technology, CD-ROM, digital optical disks or other optical storage, magnetic cassettes, magnetic tape, magnetic disk storage or other magnetic storage devices, or any other non-transmission medium that can be used to store information for access by a computing device. As defined herein, computer storage media do not consist of, and are not formed exclusively by, modulated data signals, such as a carrier wave. In contrast, communication media may embody computer-readable instructions, data structures, program modules, or other data in a modulated data signal, such as a carrier wave, or other transmission mechanism.

Memory 1340 may include programs or software procedures that, when executed by processor(s) 1310, cause computing server 1300 to perform various functions as described herein. As shown in FIG. 13, memory 1340 may include an operating system 1341, an administrative scheme 1342, a horticultural database 1343, an image analysis module 1344, a remediation module 1345, and a navigation module 1346. Operating system 1341 may include components that manage or otherwise coordinate processor(s) 1310 and hardware 1330 with software resources to perform various functions generally associated with a computer.

Administrative scheme 1342 may include various administrative items described above. Administrative scheme 1342 may include operation dashboard 300, ground robot dashboard 1000, and mission dashboard 1100. Administrative scheme 1342 may also include local area map(s) 400, physical structure map(s) 500, grow operation map(s) 600, field activity map(s) 700, RZ map(s) 800, and PU lists 1200. In an event that computing server 1300 embodies a local server (e.g., local server 121 or 122), each of the administrative items of administrative scheme 1342 may contain information regarding a particular field (e.g., field F01 or greenhouse G02). In an event that computing server 1300 embodies a central server (e.g., central server 199), each of the administrative items of administrative scheme 1342 may contain information from all the horticultural fields serviced by AHF system 100. Processor(s) 1310 may constantly update the administrative items so that administrative scheme 1342 may effectively reflect status of AHF system 100 effective in a real-time or just-in-time manner. Namely, each of the administrative items of administrative scheme 1342 may change from a moment to the next. Moreover, new missions may be added to mission dashboard 1100 by remediation module 1345 or a human worker (e.g., master grower 195 or 198 or field worker 191 or 192).

Horticultural database 1343 may store both plant-related and non-plant-related horticultural data collected by sensors of AHF system 100 via field-sensing and onboard-sensing approaches. A horticultural data entry may be recorded along with a time stamp and an identification of one or more specific plants the horticultural data is pertinent to. In an event that computing server 1300 embodies a local server (e.g., local server 121 or 122), horticultural database 1343 may store horticultural data regarding a particular field (e.g., field F01 or greenhouse G02). In an event that computing server 1300 embodies a central server (e.g., central server 199), horticultural database 1343 may store horticultural data collected from all the horticultural fields serviced by AHF system 100.

Image analysis module 1344 may include image processing algorithms or software procedures that are able to process or otherwise render still images or video recordings stored in horticultural database 1343. In some embodiments, the image processing algorithms may highlight or otherwise identify abnormal, unusual, or unique visual features thereof that may be an indication of a horticultural problem. In some embodiments, the image processing algorithms may estimate a height, a density of flower buds or fruits, a size or quantity of produces, etc., based on the still images or video recordings stored in horticultural database 1343.

Remediation module 1345 may, based on raw horticultural data stored in horticultural database 1343 or rendered image/video processed by image analysis module 1344, identify a horticultural problem. In some embodiments, remediation module 1345 may also prescribe or otherwise determine a remedial solution to address the horticultural problem. In some embodiments, the remediation solution may trigger one or more horticultural missions in AHF system 100.

Navigation module 1346 may direct or otherwise assist a ground robot to navigate to a destination, where the ground robot may perform a horticultural mission. It is to be noted that navigation module 1346 is not intended to replace the onboard positioning/navigation function of a ground robot. Rather, navigation module 1346 may work in concert with the onboard positioning/navigation function to guide the ground robot to the destination. For example, navigation module 1346 may determine, according to mission dashboard 1100, operation dashboard 300, and grow operation map 600, that ground robot av01 is required to travel to local areas A5-A7 and B5-B7 of field F04 for executing mission m10061. Using wireless transceiver 1326 of communication hardware 1320, computing server 1300 may transmit the destination information (i.e., "local areas A5-A7 and B5-B7 of field F04"), as determined by navigation module 1346, to ground robot av01 so that the onboard positioning/navigation function of ground robot av01 may navigate ground robot av01 to the destination.

In some embodiments, navigation module 1346 may determine, in addition to a destination, a path along which a ground robot may arrive at the destination. For example, firstly, navigation module 1346 may determine, according to mission dashboard 1100, operation dashboard 300, and grow operation map 600, that ground robot av04 is required to local areas A1, A2, B1 and B2 of field F04, where grow operation op512 is, for executing mission m10070. Secondly, navigation module 1346 may determine, according to ground robot dashboard 1000, that ground robot av04 is docked in ground robot bay vb01, which is located in local area A7 according to physical structure map 500. Thirdly, navigation module 1346 may identify various RZs between local area A7 and the destination using RZ map 800, and subsequently determine a path between local area A7 and local area B1 that avoids the RZs specified on RZ map 800. In particular, navigation module 1346 may determine path 910 between ground robot bay vb01 and local area B1, whereas path 910 avoids all RZs specified on RZ map 800, such as RZs 942, 943, and 944. Computing server 1300 may transmit the destination information (i.e., "local areas A1, A2, B1 and B2 of field F04"), as well as path 910, to ground robot av04 so that the onboard positioning/navigation function of ground robot av04 may navigate ground robot av04 to the destination along path 910.

Figure 14:
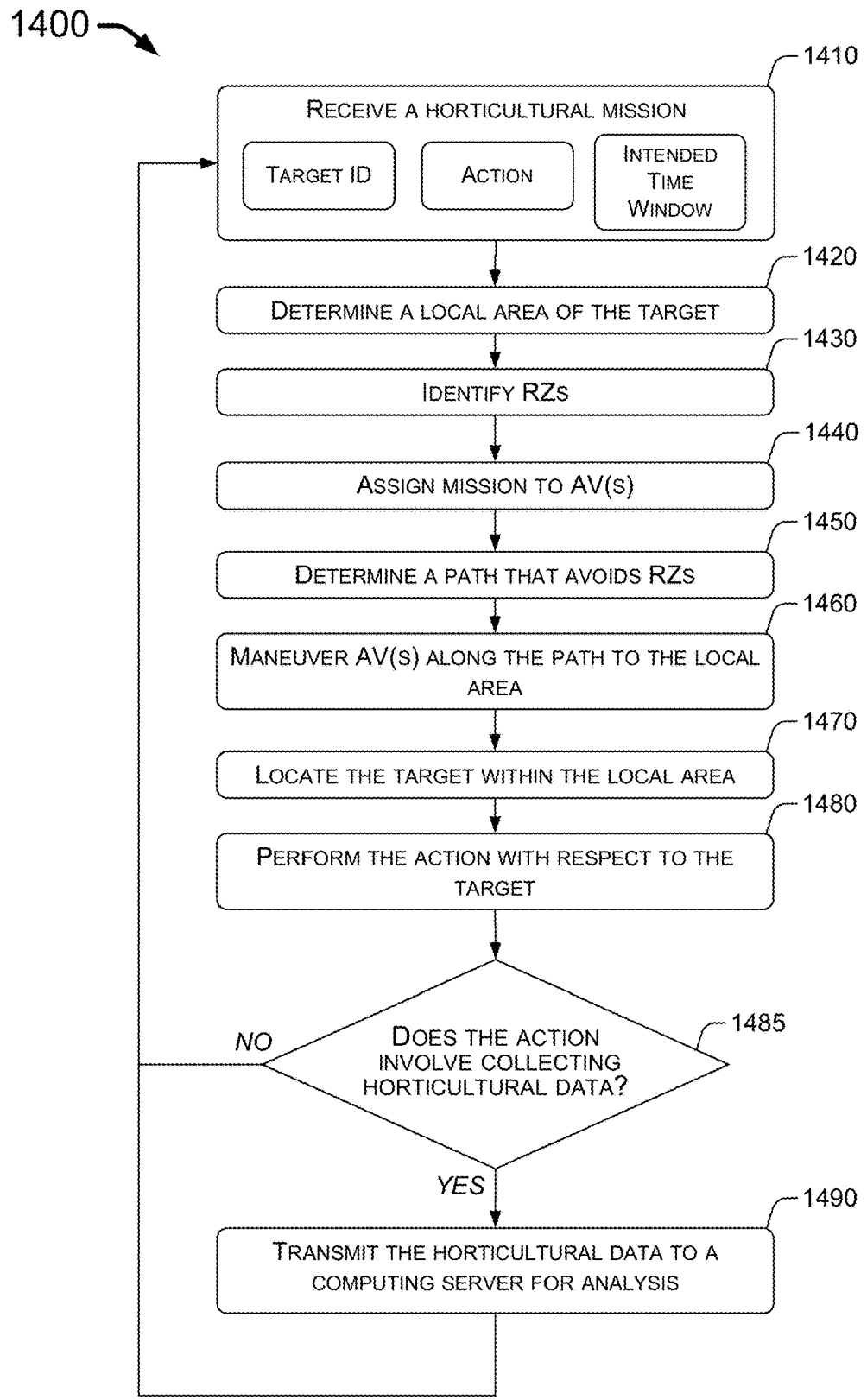
FIG. 14 illustrates a flow diagram of an example process for executing a horticultural mission of an AHF process.
Figure 15:
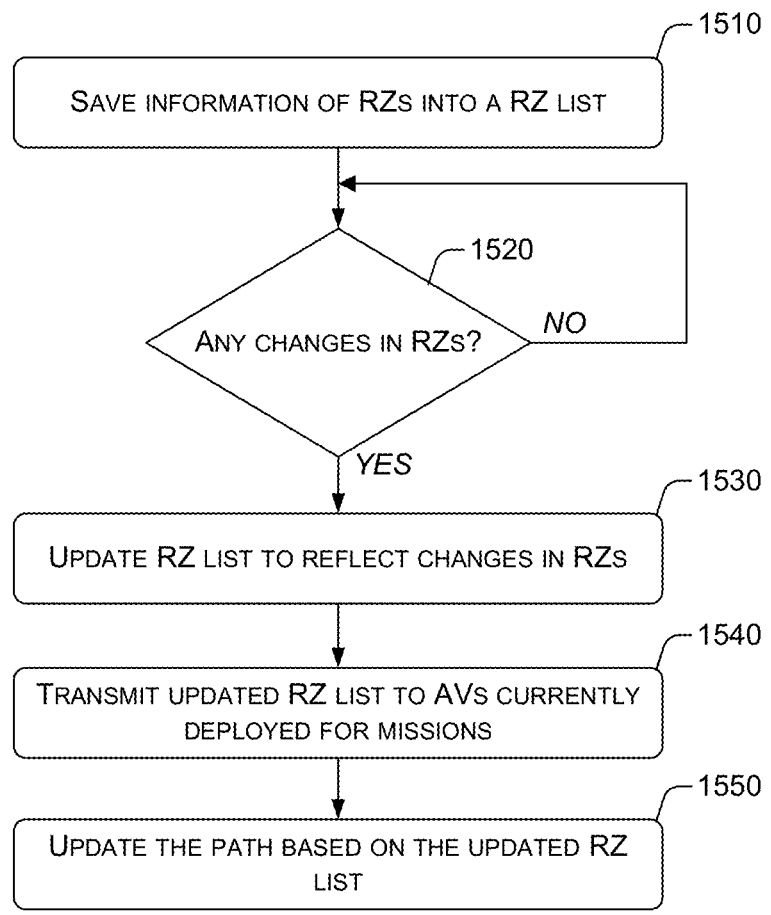
FIG. 15 illustrates a flow diagram of an example process for updating a path.

FIG. 14 and FIG. 15 present illustrative processes 1400 and 1500, respectively. Process 1400 provides a method for executing a horticultural mission of an AHF process, whereas process 1500 provides a method for dynamically updating a ground robot path as NRZs change. Each of processes 1400 and 1500 is illustrated as a collection of blocks in a logical flow chart, which represents a sequence of operations that can be implemented in hardware, software, or a combination thereof. In the context of software, the blocks represent computer-executable instructions that, when executed by one or more processors, perform the recited operations. Generally, computer-executable instructions may include routines, programs, objects, components, data structures, and the like that perform particular functions or implement particular abstract data types. The order in which the operations are described is not intended to be construed as a limitation, and any number of the described blocks can be combined in any order and/or in parallel to implement the process. For discussion purposes, the processes 1400 and 1500 are described with reference to FIGS. 1-13.

FIG. 14 is a flow diagram of an example process 1400 for executing a horticultural mission of an AHF process. The horticultural mission may involve performing a certain horticultural action to a target (e.g., a plant) located within a horticultural field. The horticultural mission may be assigned to a ground robot that is physically away from the target, and the ground robot may travel to the target, while avoiding various RZs along the way, to perform the action. Depending on the essence of the mission, some results may be collected by the ground robot, such as certain horticultural data pertinent to the target. The ground robot may transmit the horticultural data, either directly or indirectly, to a computing server in a real-time or just-in-time manner for further analysis. Process 1400 may include blocks 1410, 1420, 1430, 1440, 1450, 1460, 1470, 1480, 1485 and 1490. Process 1400 may begin at block 1410.

At block 1410, server 1300 may receive a horticultural mission. The mission may be entered into AHF system 100 by master grower 198. The mission may be listed in mission dashboard 1100, such as mission m10080 therein. The horticultural mission may include an identification of a target located within a horticultural field. The mission may also include an action to be performed with respect to the target. For example, as shown in mission dashboard 1100, mission m10080 includes a target ID (i.e., pu_1231), as well as an action to be performed with respect to the target (i.e., collect soil pH level).

In some embodiments, a mission may also include an intended time window, wherein the action is intended to be performed with respect to the target within the intended time window. For example, mission dashboard 1100 records that mission m10080 has an intended time window between 20:00 and 21:00 on May $22^{nd}$. That is, mission m10080 intends to collect the soil pH level regarding a target having a target ID pu_1231 between 20:00 and 21:00 on May $22^{nd}$. The intended time window is specified in the mission for the sake of validity of the horticultural process involving the mission. For example, the action of the mission may involve collecting certain horticultural data with respect to the target, and the action has to be performed within a specific time frame (i.e., the intended time window) so that the horticultural data as collected may be valid or meaningful for the subsequent analysis of the horticultural data. Process 1400 may proceed from block 1410 to block 1420.

In some embodiments, there may be a difference in time between the completion of block 1410 and the start of block 1420, notably in an event that the mission includes an intended time window, as explained below. Process 1400 aims to perform the action with respect to the target while the target remains stationary within the horticultural field. Due to horticultural activities, PUs of a horticultural field may experience frequent changes in locations within the horticultural field. This is not an uncommon scenario especially when the horticultural field is a greenhouse, as plants growing in a greenhouse may often need to be moved around for horticultural and logistic purposes. In an event that a mission includes an intended time window, a difference in time between the completion of block 1410 and the start of block 1420 may be required, so that the AHF system may perform the horticultural mission while the target is not having a location change. Specifically, server 1300 may determine an immobile duration within the intended time window. During the immobile duration, the target PU is not scheduled to have a location change. Moreover, server 1300 may wait until an onset of the immobile duration arrives before proceeding to block 1420. This is to ensure that the mission does not start to execute until the target is not subject to a scheduled location change.

For example, mission dashboard 1100 indicates that mission m10080 is intended to be executed between 20:00 and 21:00 on May $22^{nd}$. The target of mission m10080 is PU pu_1231. Based on the identification of the target, an immediate location of PU pu_1231 may be looked up in PU lists 1200, and thus determined as in local area A1 of field F04. Field activity map 700 may indicate that PUs in local area A1 of field F04 are scheduled to relocate, on May $22^{nd}$, to local area A4 for six hours and then back to local area A1, and the relocation is not scheduled to finish until 20:30 on May $22^{nd}$. Server 1300 may thus determine that an immobile duration for mission m10080 is 20:30-21:00 on May $22^{nd}$.

At block 1420, server 1300 may determine, based on the identification of the target, a local area of the horticultural field, wherein the target is located within the local area. For example, by looking up target ID pu_1231 in PU lists 1200, server 1300 may determine that the target is located within local area A1 of field F04. Process 1400 may proceed from block 1420 to block 1430.

At block 1430, server 1300 may identify one or more RZs within the horticultural field. For example, server 1300 may access RZ map 800, which identifies a plurality of RZs within field F04. Process 1400 may proceed from block 1430 to block 1440.

At block 1440, server 1300 may assign the mission to at least one of a plurality of ground robots servicing the horticultural field. For example, as recorded in mission dashboard 1100, server 1300 may assign mission m10080 to ground robot av03. Namely, the identification of the target (i.e., PUID pu_1231) and the action (i.e., collect a pH level measurement reading of the soil) are both made known to ground robot av03.

In some embodiments, block 1440 may be implemented in several sequential steps. Firstly, block 1440 may involve server 1300 determining a quantity of ground robots needed for performing the mission. For most horticultural missions, such as mission m10080, a single ground robot may be enough. However, depending on the action to be performed in a mission, two or more ground robots may be required. For example, a mission may intend to cover a local area with a shade screen of a rectangle shape. The mission would be extremely difficult to execute if using only one ground robot. Server 1300 may determine that four ground robots are needed to execute the mission, with one ground robot carrying a respective corner of the shade screen.

Secondly, block 1440 may involve server 1300 determining resources needed for the mission. For example, server 1300 may determine that, in order to carry the shade screen, each of the four ground robots needs to have a payload of at least 5 lbs.

Thirdly, block 1440 may involve server 1300 performing a resource check on ground robots until a number of ground robots equal to or exceeding the quantity of ground robots needed pass the resource check. For example, server 1300 may check the ground robots listed in ground robot dashboard 1000 until four ground robots each having a payload of 5 lbs or more are identified. Assuming all ground robots listed in ground robot dashboard 1000 are available for the moment, server 1300 may perform a resource check by checking the payload specification of the ground robots. Server 1300 may subsequently determine that ground robots av01, av05, av06 and av07 pass the resource check, as each of the four ground robots has a payload that is at least 5 lbs. When performing the resource check, server 1300 may preferably check the ground robots that are closer to the target. Specifically, server 1300 may begin with a ground robot that is located closest to the target, and then continue with other ground robots based on a distance between the respective ground robot and the target in an ascending order. Namely, server 1300 may start from a ground robot that is located the closest to the target to see if the specific ground robot passes the resource check. Server 1300 may then perform the resource check on a ground robot that is second closest to the target. Server 1300 may then continue the resource check with the third closest ground robot from the target, the fourth closest ground robot, the fifth closest ground robot, and so on, until ground robots of the needed quantity have passed the resource check. This approach may ensure the ground robots executing the mission are located relatively close to the target of the mission.

Fourthly, block 1440 may involve server 1300 assigning the mission to the number of ground robots that pass the resource check. For example, server 1300 may assign the mission of cover the local area with the shade screen to ground robots av01, av05, av06 and av07. Process 1400 may proceed from block 1440 to block 1450.

At block 1450, server 1300 may determine, for the ground robot (or each of the ground robots) to which the mission is assigned, a path along which the ground robot may travel to the target. Specifically, the path is required to avoid RZs as specified in RZ map 800. As an example, path 910 is determined for ground robot 920 to move along, whereas path 910 avoids RZs 941-946. Process 1400 may proceed from block 1450 to block 1460.

At block 1460, server 1300 may maneuver the ground robot (or each of the ground robots) along the path determined at block 1450 to the local area determined at block 1420. Specifically, navigation module 1346 of server 1300 may notify the ground robot (or each of the ground robots) about the destination (i.e., the local area) determined at block 1420 as well as the path determined at block 1450. The ground robot (or each of the ground robots) may maneuver itself along the path to the destination using the onboard positioning/navigation functions or an external positioning mechanism such as positioning mechanism 200. For example, using positioning mechanism 200, ground robot av03 may follow the path determined at block 1420 to arrive at local area A1 of field F04. As described above, the ground robot may travel along the path within a certain proximity (e.g., ground robot 920 traveling along path 910 within a range of proximity 911). In some embodiments, the ground robot can move to follow the path within predetermined tolerances or bounds, for example diverting no more than a predetermined or assigned distance from a center of the path (which can be defined as a line), such as plus or minus three feet laterally or vertically. The path can also be defined as a continuous airspace region through which the ground robot is authorized to travel, and parameters can be set so that the ground robot travels through the region or path while maintaining predetermined distances from lateral boundaries of the region. Limits can be defined proportionally (e.g., staying within a central third of any confining dimension of the path) and/or discretely (e.g., no closer than three feet to any path boundary), and can appropriately vary along the path according to various conditions such as obstacles, prevailing winds, or other hazards. Process 1400 may proceed from block 1460 to block 1470 after the ground robot (or each of the ground robots) arrives at the destination.

At block 1470, the ground robot (or each of the ground robots) may locate the target within the local area. For example, in executing mission m10080, ground robot av03 may, after arriving at local area A1 of field F04, locate the target within local area A1 by scanning one or more of PU labels 1213, 1223, 1233, 1243, 1253, 1263, 1273 and 1283. Specifically, upon scanning PU label 1233, ground robot av03 may recognize that PU label 1233 reveals PUID pu_1231, which matches the identification of the target of mission m10080. Therefore, ground robot av03 may locate the plant growing in PU 1232 to be the target of mission m10080. Process 1400 may proceed from block 1470 to block 1480.

At block 1480, the ground robot(s) may perform the action with respect to the target. Some missions may not involve an action of collecting horticultural data pertinent to the target, whereas some other missions may. For example, ground robot av03 may collect a pH level reading of the soil of PU 1232 by receiving the pH level reading from a pH meter embedded in the soil of PU 1232. ground robot av03 may receive the pH level reading using a low-power/short-range wireless communication technology while maneuvering near PU 1232. ground robot av03 may temporarily store the pH level reading in an onboard memory of ground robot av03. Process 1400 may proceed from block 1480 to block 1485.

At block 1485, server 1300 may determine the status of the ground robot(s) based on whether the action involves collecting horticultural data. In an event that the action does not involve collecting horticultural data, process 1400 may proceed from block 1485 to 1410. That is, the ground robot(s) have completed the mission and are ready to be assigned a new mission. In an event that the action involves collecting horticultural data, process 1400 may proceed from block 1485 to 1490.

At block 1490, a ground robot may, after performing the action of the mission, transmit the horticultural data as collected to a computing server for further analysis. For example, as part of the execution of mission m10080, ground robot av03 may transmit the soil pH level reading pertinent to PU 1232, as collected, to a local area server of field F04 for analysis. In some embodiments, server 1300 may maneuver the ground robot to a data transfer bay (i.e., a vehicle bay that serves as a data transfer station), where the ground robot may transfer the horticultural data as collected to a storage device located at the data transfer bay. The horticultural data may be transmitted from the storage device at the data transfer bay to a computing server for analysis. For example, in executing a horticultural mission, a ground robot 132 may take still images of grow operation 103 of greenhouse G02, and save the still images in an onboard memory of the ground robot 132. The ground robot 132 may then travel to vehicle bay 142, which may be a data transfer bay. The ground robot 132 may then transfer the still images of grow operation 103 from the onboard memory to a storage device of vehicle bay 142. Subsequently, the still images of grow operation 103 stored at the storage device of vehicle bay 142 may be uploaded to local server 122 and saved in horticultural database 1343 of local server 122 using wired or wireless communication techniques. The still images of grow operation 103 may then be processed and analyzed by image analysis module 1344 and remediation module 1345 to identify possible horticultural issues of grow operation 103. Process 1400 may proceed from block 1490 to 1410.

In some embodiments, blocks 1480, 1485 and 1490 may not necessarily occur in sequence. Instead, blocks 1480, 1485 and 1490 may in some respects occur concurrently, either in parallel or in an overlapping fashion. For example, a horticultural mission assigned to a ground robot 131 may involve an action of taking live video recording of grow operation 102 as irrigation robot 161 moves along and irrigates grow operation 102. The ground robot 131 may, while in the process of recording, wirelessly transmit the recorded video footage to a storage device of a vehicle bay 141 in a real-time manner. Master grower 198 may real-time monitor the irrigation process shown on user device 197 by accessing the video footage stored in the storage device via network 196 and the communication link between local server 121 and the vehicle bay 141. The video footage may be transmitted to central server 199 for further analysis or storing a copy. In an event that the ground robot 131 cannot establish a direct wireless communication link to the vehicle bay 141 (e.g., the ground robot 131 being too far away from the vehicle bay 141 and thus out of a communication range), one or more other ground robots 131 may be deployed to establish an airborne communication link, via which the video footage may be passed from one ground robot 131 to the next ground robot 131 and eventually to the storage device of the vehicle bay 141.

In some embodiments, a ground robot may execute multiple missions before the ground robot transmits the collected horticultural data. This is particularly the case if AHF system 100 does not need the horticultural data immediately or soon. Namely, horticultural data collected from several missions may be all be temporarily stored in an onboard memory of the ground robot, and then be transmitted to a computing server for analysis at a later time.

FIG. 15 is a flow diagram of an example process 1500 for dynamically updating a ground robot path as RZs changes. Process 1500 may be applied or otherwise combined with process 1400 to enhance the respective process by providing resilience of a ground robot path in the face of RZ changes. Process 1500 may include blocks 1510, 1520, 1530, 1540 and 1550. Process 1500 may begin at block 1510.

At block 1510, server 1300 may save information regarding RZs specified on RZ map 800 into a corresponding RZ list. RZ map 800 and the corresponding RZ list contain essentially the same information, i.e., where the RZs are defined in a horticultural field at the moment. Process 1500 may proceed from block 1510 to block 1520.

At block 1520, server 1300 may compare a current version of the RZ list with an immediately previous version of the RZ list to find any incremental change in the RZs specified thereon. In an event that server 1300 finds no change in RZs between the two versions, process 1500 may stay at block 1520. In an event that a change in RZs is found, process 1500 may proceed from block 1520 to block 1530.

At block 1530, server 1300 may update the RZ list according to the most recent RZ map 800 to reflect the change(s) in RZs. Process 1500 may proceed from block 1530 to block 1540.

At block 1540, server 1300 may transmit the updated RZ list to ground robots that are currently deployed for missions. Namely, each ground robot that is currently deployed for a mission may receive a copy of the most recent RZ list. Process 1500 may proceed from block 1540 to block 1550.

At block 1550, each airborne ground robot may check whether the path that it is currently traveling along may interfere with the RZs specified in the most recent RZ list. In an event that the current path may interfere with an RZ therein, the positioning/navigation functions of the ground robot may update the path to avoid all RZs specified in the most recent RZ list. Alternatively, navigation module 1346 of server 1300 may update the path based on the most recent RZ list and send the updated path to the ground robot to follow along.

Figure 16:
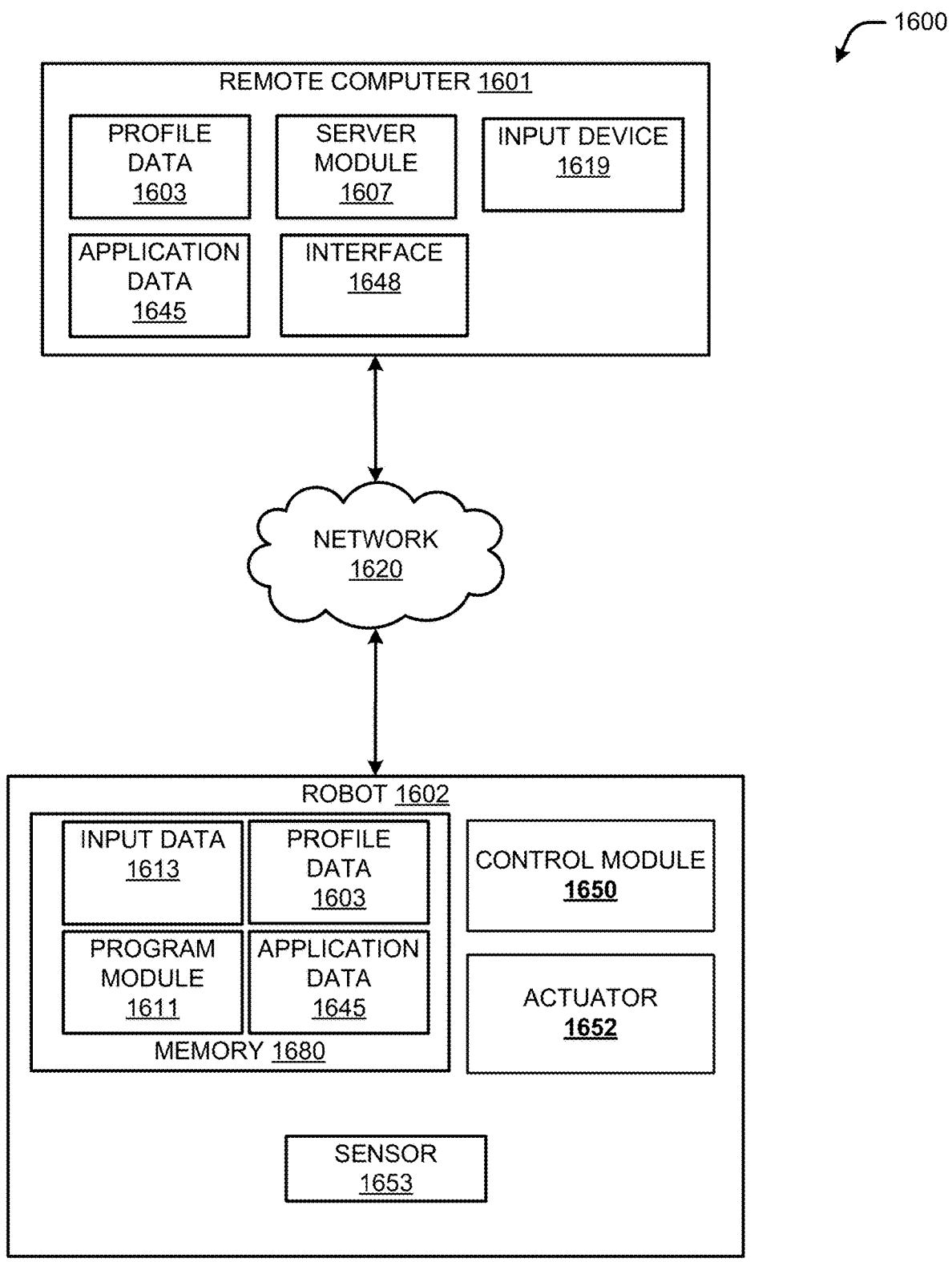
FIG. 16 is a block diagram showing various components of an example autonomous vehicle.

FIG. 16 is a system diagram showing aspects of one illustrative system disclosed herein for servicing horticultural fields using ground robots. As shown in FIG. 16, a system 1600 may include a remote computer 1601, an autonomous device 1602, and a network 1620. For illustrative purposes, the autonomous device 1602 is also referred to herein as a "autonomous vehicle 1602" "ground robot 1602" or a "robot 1602" or a "second computing device 1602." It should be understood that some or all of the functions and components associated with autonomous device 1602 and remote computer 1601 may be implemented on a single device or multiple devices.

The remote computer 1601 and the robot 1602 may be interconnected through one or more local and/or wide area networks, such as the network 1620. In addition, the robot 1602 may be in communication with the remote computer 1601 and other computers by the use of one or more components. For instance, the robot 1602 may be equipped with one or more light sources, and the remote computer 1601 may include one or more sensors, including a camera, for detecting the location of the robot 1602. As will be described in more detail below, the robot 1602 may be configured with light sources, sensors and transmitting devices to facilitate communication with one or more devices. Other wired or wireless communication mechanisms may be utilized to provide communication between one or more components and/or devices shown in FIG. 16 and other components or computers. In some configurations, the robot 1602 can also include an input device, a sensor, such as a camera, or other devices for generating image data or input data 1613. Any data obtained or generated by the robot 1602 can be communicated to another computer or device, such as the remote computer 1601. It should be appreciated that many more network connections may be utilized than illustrated in FIG. 16.

The remote computer 1601 may be in the form of a personal computer, a server, a laptop, or any other computing device having components for causing a display of one or more images on a display, such as an interface 1648. In one illustrative example, the interface 1648 may include a screen configured to provide a graphical user interface.

The remote computer 1601 may comprise a sensor 1653, such as a sonar sensor, a depth sensor, infrared sensor, heat sensor, touch sensor, or any other device or component for detecting the presence, position, and/or characteristics of an object. In addition, the remote computer 1601 can comprise an input device 1619, such as a keyboard, mouse, microphone, or any other device configured to generate a signal and/or data based on any interaction with the remote computer 1601. For illustrative purposes, signals or data provided by a component, such as the sensor 1653 or the input device 1619 is referred to herein as input data 1613. Input data 1613 may also include contextual data or other data received from a computing system, such as the remote computer 1601, or a server providing a resource or service.

The robot 1602 may include a local memory 1680 that stores profile data 1603, input data 1613, and application data 1645. The profile data 1603 may store information describing user activity, preferences and other information used for providing control of robot 1602. The application data 1645 may include output data generated by techniques disclosed herein.

The robot 1602 may also include a program module 1611 configured to manage techniques described herein and interactions between a robot and the remote computer 1601. For example, the program module 1611 may be configured with one or more surface reconstruction algorithms and other algorithms for locating objects and devices. The surface reconstruction algorithms and other algorithms may use data or signals collected from one or more sensors 1653, such as a depth sensor attached to the robot 1602.

The robot 1602 may be equipped with a control module 1650 for executing instructions communicated to the robot 1602. The robot 1602 may have one or more control components, such as an actuator 1652. Components of the robot 1602, such as the actuator 1652, may be configured to generate a physical movement of one or more objects from instructions received by the robot 1602. Robot 1602 may also comprise a number of motors configured to control the movement of the robot 1602.

In some aspects of the disclosure, the robot 1602 detects one or more conditions based on the input data 1613 and other data and generates one or more instructions for controlling the robot 1602. In some configurations, the robot 1602 obtains input data 1613 and other data describing the location and status of the robot 1602. In addition, the robot 1602 may obtain and process data indicating a location of the robot 1602 relative to the remote computer 1601.

Any input data 1613 received from any resource, such as a remote computer or a sensor, may be used by the robot 1602 to determine the location of any object, the location of the remote computer 1601 and the location of the robot 1602. For instance, the robot 1602 may include one or more sensors for obtaining depth map data, such as a depth sensor, and other data to identify the location of various objects in a room, including the room boundaries. Configurations disclosed herein can generate data describing geometric parameters of any object or boundary.

Any known technology for identifying the location of one or more objects may be used by the techniques disclosed herein. In one example, data defining the location of the robot 1602 or a person may be obtained by the use of an optical sensor, such as a camera or any other sensor 1653 or input device 1619, and lights or other visual elements mounted on the robot 1602.

These examples are provided for illustrative purposes only and are not to be construed as limiting. Any technology may be used for identifying a location of any computing device or object, which may involve the use of a radio signal, a light-based signal or any signal capable of identifying the location of an object. The robot 1602 may process any input data 1613 from any device or resource to identify the location and other contextual information regarding objects or computing devices.

In some configurations, the robot 1602 may have one or more sensors for capturing and generating data. In one illustrative example, the robot 1602 may be equipped with one or more depth map cameras. The depth map cameras, or any other type of sensor, may collect data describing objects detected by the sensors. In yet another example, the robot 1602 may be equipped with a wheel position sensor. Data or a signal generated by such sensors, such as the wheel position sensor, may be used to identify the location, velocity or other information regarding the robot 1602. These examples are provided for illustrative purposes only and are not to be construed as limiting. It can be appreciated that a number of sensors or devices may be used to generate/obtain data associated with one or more objects and to identify the location of one or more objects.

The obtained data, such as depth map data, may be then processed to identify objects and the location of objects, and to generate and display data associated with the object. In some embodiments, the data associated with the object may be displayed on a user interface with a representation or graphical element that shows an association between the data associated with the object and an object. For illustrative purposes, data that is associated with an object is referred to herein as "attached data" or data that is "attached" to an object. In addition, any obtained data, also referred to herein as input data 1613, may be used for generating and modifying instructions for the robot 1602. In some configurations, robot 1602 can be configured to perform or manage complex navigation and pathfinding tasks.

In some configurations, the robot 1602 interprets input data 1613 and/or other data to determine a context with respect to objects in its vicinity. The robot 1602 may perform one or more functions, such as a depth map analysis and surface reconstruction analysis to identify objects and properties of objects. For instance, certain geometric shapes and other parameters, such as a size of an object, may be used to categorize or characterize individual objects, e.g., an object may be characterized as "fence," a "high-priority object," or a "primary object." Other data related to objects in an environment may be obtained from databases or other resources.

In some configurations, the robot 1602 may process input data 1613 from one or more resources to generate contextual data. The contextual data can be used to identify a location associated with each identified object. Based on location information, other data, and other properties associated with each object, the robot 1602 can generate instructions to perform one or more tasks. The generated instructions may be based on the location of the identified objects, such as a computer, geometric data, characteristics of an object, and other contextual information.

To illustrate aspects of the techniques disclosed herein, consider a scenario where the robot 1602 is in an environment, e.g., a field, with other objects. Sensors 1653 and input devices 1619 can generate signals or data associated with the objects. For instance, the signals or data can be processed by one or more methods, such as technologies involving triangulation algorithms, to identify the location of the objects and/or the robot 1602. Other input data 1613 may be received and processed with the signals or data to identify the location of the objects and/or the robot 1602 and other parameters, such as the size and shape of the objects and/or the robot 1602. Processing can be applied to any received data or signal to identify the location and geometric properties of objects in the vicinity. The obtained information can be used to generate one or more instructions that may be processed by the robot 1602 for execution. The instructions enable the robot 1602 to perform one or more tasks, which may involve interaction between the robot 1602 and one or more objects in the room.

The ability for a horticultural feedback system to employ robots, including ground robots, to aid in horticultural feedback processes provides tremendous benefits in terms of cost, efficiency, and effectiveness, as compared to traditional horticultural feedback systems that heavily rely on human labor. A coherent administrative scheme providing real-time or just-in-time marshaling of information regarding AHF activities is crucial to the performance of an AHF system. Thanks to the administrative scheme, horticultural missions may be optimally assigned to, and executed by, ground robots equipped with various cameras, sensors, and other resources. Furthermore, RZs may be comprehensively identified and updated based at least on types of grow operations, physical structures in the field, horticultural activities being conducted, weather, technical specifications of ground robots, which contributes to safe and efficient operation of ground robots.

The disclosure presented herein encompasses the subject matter set forth in the following example clauses.

Example 1

A method for servicing a horticultural operation comprising one or more local areas, the method comprising:
receiving, by a computing system, data from one or more autonomous vehicles, the data pertaining to the horticultural operation or one or more targets located within the horticultural operation;
analyzing the received data to determine one or more conditions of the one or more targets;
based on the analyzing, determining one or more recommendations for addressing the one or more conditions;
sending the determined conditions and recommendations to a user interface;
when authorized, transmitting data to the one or more autonomous vehicles that are indicative of follow-on actions for the target; and
receiving additional data, when available, based on the follow-on actions for further analysis.

Example 2

The method of example 1, wherein the analyzing comprises stitching together a set of images, isolating one or more local areas from the stitched image, and analyzing the isolated local areas Example 3

The method of example 1, further comprising receiving sensor data from one or more sensors configured to capture data pertaining to the target.

Example 4

The method of example 3, wherein the one or more sensors include environmental sensors or image capturing devices, wherein the environmental sensors including at least one of range-finding sensors, light intensity sensors, light spectrum sensors, non-contact infra-red temperature sensors, thermal sensors, photoelectric sensors that detect changes in color, carbon dioxide uptake sensors, water, pH testing, and oxygen production sensors, and wherein the image capturing devices comprise RGB, hyperspectral, thermal, or LIDAR imaging devices.

Example 5

The method of example 3, wherein the sensors are coupled to non-vehicles to augment the captured data.

Example 6

The method of example 1, wherein the local area comprises a plurality of plant units, wherein the target is a plant unit or a group of plant units.

Example 7

The method of example 1, wherein the data comprises one of:
a composite image of the target or an area surrounding the target;
an image of the target;
an estimated height of the target;
a 3D surface mesh analysis of the target;
estimated volume of the target;
a temperature reading in a vicinity of the target;
a humidity reading in a vicinity of the target;
an illumination reading in a vicinity of the target;
a pH level of soil or water in which the target is planted;
a physical sample of the target;
a germination state of the target;
canopy coverage of the target;
canopy growth of the target;
flower/bud count of the target;
disease or anomaly regions of the target;
estimated vapor pressure deficit (VPD) of leaves of the target;
estimated temperature of leaves of the target; or flower/bud density of the target.

Example 8

The method of example 1, wherein the determining one or more recommendations is performed by a machine learning component.

Example 9

The method of example 1, wherein the one or more recommendations include at least one of changing a light intensity or a light spectrum of lighting, changing an amount of water or a frequency of a watering operation, changing an amount of nutrients or fertilizer, changing a ratio of nutrients to fertilizer, changing an airflow, changing a temperature, changing an airflow intensity, changing an airflow direction schedule, or changing an automated spraying of pesticides.

Example 10

The method of example 1, further comprising determining a progress metric of the target, the progress metric indicative of progress of the target relative to predetermined milestones.

Example 11

The method of example 10, wherein the analyzing comprises determining that the progress metric is not meeting the predetermined milestones; wherein the one or more recommendations comprise generating one or more actions to improve the progress.

Example 12

The method of example 1, wherein the follow-on actions include actions for automation of at least one plant grower action for the target.

Example 13

A system, comprising:
one or more processors;
memory having instructions stored therein, wherein the instructions, when executed by the one or more processors, cause the system to:
receive data from one or more autonomous vehicles, the data pertaining to a horticultural operation or one or more targets located within the horticultural operation;
analyze the received data to determine one or more conditions of the one or more targets;
based on the analyzing, determine one or more recommendations for addressing the one or more conditions;
send the determined conditions and recommendations to a user interface;
when authorized via the user interface, transmit data to the one or more autonomous vehicles that are indicative of follow-on actions for the target; and
receive additional data, when available, based on the follow-on actions for further analysis.

Example 14

The system of example 13, further comprising instructions stored therein, wherein the instructions, when executed by the one or more processors, cause the one or more processors to receive sensor data from one or more sensors configured to capture data pertaining to the target.

Example 15

The system of example 13, wherein the data comprises one of:
a composite image of the target or an area surrounding the target;
an image of the target;
an estimated height of the target;
a 3D surface mesh analysis of the target;
estimated volume of the target;
a temperature reading in a vicinity of the target;
a humidity reading in a vicinity of the target;
an illumination reading in a vicinity of the target;
a pH level of soil or water in which the target is planted;
a physical sample of the target;
a germination state of the target;
canopy coverage of the target;
canopy growth of the target;
flower/bud count of the target;
disease or anomaly regions of the target;
estimated vapor pressure deficit (VPD) of leaves of the target;

estimated temperature of leaves of the target; or flower/bud density of the target.

Example 16

The system of example 13, wherein the determine one or more recommendations is performed by a machine learning component.

Example 17

A computer-readable medium comprising instructions stored therein, wherein the instructions, when executed by a system comprising one or more processors, cause the system to:
receive data from one or more autonomous vehicles, the data pertaining to a horticultural field or one or more targets located within the horticultural field;
analyze the received data to determine one or more conditions of the one or more targets;
based on the analyzing, determine one or more recommendations for addressing the one or more conditions;
send the determined conditions and recommendations to a user interface;
transmit data to the one or more autonomous vehicles that are indicative of follow-on actions for the target; and
receive additional data, when available, based on the follow-on actions for further analysis.

Example 18

The computer-readable medium of example 17, wherein the one or more recommendations include at least one of changing a light intensity or a light spectrum of lighting, changing an amount of water or a frequency of a watering operation, changing an amount of nutrients or fertilizer, changing a ratio of nutrients to fertilizer, changing an airflow, changing a temperature, changing an airflow intensity, changing an airflow direction schedule, or changing an automated spraying of pesticides.

Example 19

The computer-readable medium of example 17, further comprising determining a progress metric of the target, the progress metric indicative of progress of the target relative to predetermined milestones; wherein the analyzing comprises determining that the progress metric is not meeting the predetermined milestones; wherein the one or more recommendations comprise generating one or more actions to improve the progress.

Example 20

The computer-readable medium of example 16, wherein the follow-on actions include actions for automation of at least one plant grower action for the target.

The disclosure presented herein encompasses the subject matter set forth in the following example clauses.

Example 1

A method implementable to a horticultural operation comprising one or more local areas, the method implemented by a system configured to autonomously interact with the horticultural operation, the method comprising:
autonomously identifying the horticultural operation or a target located within the horticultural operation and an action to be performed with respect to the horticultural operation or target, the operation or target comprising at least one plant or a group of plants;
determining, based on the identifying, a local area of the horticultural operation, wherein the target is located within the local area;
associating the horticultural operation or target to at least one autonomous vehicle;
locating, by the at least one autonomous vehicle, the horticultural operation or target within the local area; and
performing the action with respect to the horticultural operation or target by the at least one autonomous vehicle.

Example 2

The method of example 1, further comprising determining a path between the at least one autonomous vehicle and the local area, the path avoiding one or more restricted zones; wherein each of the one or more restricted zones is continuous and comprises at least a portion of the local area.

Example 3

The method of example 2, further comprising using 3D data to map obstacles.

Example 4

The method of example 2, wherein the one or more restricted zones comprises one of the following:
a portion of the local area above a first altitude or below a second altitude;
a portion of the local area at a ground level; or an identified object within the local area.

Example 5

The method of example 2, wherein the one or more restricted zones are determined based on one or more of the following:
a custom master grower defined region;
a height of a growing plant within a local area;
a location of a physical structure;
a local area currently having a horticultural activity;
a passage reserved for ground traffic;
an air corridor reserved for aerial traffic;
an area in which flying is restricted by a regulation; or a weather condition.

Example 6

The method of example 1, further comprising:
determining a quantity of autonomous vehicles needed for performing a mission;
performing a resource check for autonomous vehicles until a number of autonomous vehicles equal to or exceeding the quantity pass the resource check; and
assigning the mission to the number of autonomous vehicles.

Example 7

The method of example 1, further comprising:
determining a set of sub-tasks and a corresponding quantity of autonomous vehicles needed for performing a mission;
performing a resource check on available autonomous vehicles;
dynamically assigning a sub-task to available autonomous vehicles that pass a resource check; and
continuing to assign sub-tasks as autonomous vehicles become available until all sub-tasks of the set of sub-tasks have been completed.

Example 8

The method of example 6, wherein the performing of the resource check is performed in parallel or begins with one of the autonomous vehicles that is located closest to the target and continues with others of the autonomous vehicles based on a distance between the respective autonomous vehicle and the target.

Example 9

The method of example 1, wherein:
the at least one autonomous vehicle is maneuvered based on one or more of GPS, GLONASS, RTK, inertial navigation, or visual odometry.

Example 10

The method of example 1, wherein:
a plurality of beacons is disposed within the horticultural field; and
the beacons are located at defined 3D positions and emits a respective signal, the signal comprising a self-identifying RF signal, temporal or spatial visual patterns that can be captured by a camera, and wherein the signal is usable by an autonomous vehicle to determine a location or a path.

Example 11

The method of example 1, wherein QR identification devices are disposed in known positions within the horticultural field, and the autonomous vehicles are configured to compute a position based on known positions of the QR identification devices.

Example 12

The method of example 1, wherein the local area comprises a plurality of plant units, wherein the target is a plant unit or a group of plant units, wherein each of the plant units or group of plant units is associated with a machine-readable code, and wherein the locating of the target within the local area comprises scanning the machine-readable code of the plant unit or group of plant units.

Example 13

The method of example 12, wherein the machine-readable code is used to define one or more boundaries of the local area and identify the local area.

Example 14

The method of example 1, wherein the action comprises collecting horticultural data pertinent to the target, the method further comprising one or more of:
transmitting the horticultural data to a system for analysis after the action is performed; or performing the analysis on the autonomous vehicle.

Example 15

The method of example 1, wherein the action comprises collecting horticultural data pertinent to the target, the method further comprising one or more of:
maneuvering the at least one autonomous vehicle to a data transfer bay after the action is performed and transferring the horticultural data collected by the at least one autonomous vehicle to a storage device located at the data transfer bay; or wirelessly transmitting the horticultural data to a data transfer station, a Wifi network, or to a cell tower.

Example 16

The method of example 15, wherein the horticultural data comprises one of the following:
a composite image of the target or an area surrounding the target;
an image of the target;
an estimated height of the target;
a mesh analysis of the target;
estimated volume of the target;
a temperature reading in a vicinity of the target;
a humidity reading in a vicinity of the target;
an illumination reading in a vicinity of the target;
a pH level of soil or water in which the target is planted;
a physical sample of the target;
a germination state of the target;
canopy coverage of the target;
canopy growth of the target;
flower/bud count of the target; or disease or anomaly regions of the target.

Example 17

The method of example 15, further comprising determining that the target and only the target is in the horticultural data.

Example 18

A system, comprising:
a vehicle bay hosting a plurality of autonomous vehicles one or more processors;
memory having instructions stored therein, wherein the instructions, when executed by the one or more processors, cause the one or more processors to:
identify horticultural operation or a target located within the horticultural operation and an action to be performed with respect to the horticultural operation or the target, the operation or target comprising at least one plant or a group of plants;
determine, based on the identification, a local area of the operation or target;
assign the target to at least one autonomous vehicle of the plurality of autonomous vehicles;
locate, by the at least one autonomous vehicle based on the identification, the local area;
and perform the action with respect to the operation or target by the at least one autonomous vehicle.

Example 19

The system of example 18, further comprising a plurality of cameras disposed across the horticultural field, each of the plurality of cameras capable of monitoring one or more of the local areas and providing image data to the autonomous vehicles or the system.

Example 20

An autonomous vehicle configured to:
interact with a horticultural operation;
identify the horticultural operation or a target located within the horticultural operation and an action to be performed with respect to the operation or target;
locate, based on the identification, the operation or target; and
perform the action with respect to the target;
wherein the action comprises capturing data usable to autonomously analyze conditions for one or more plants within the horticultural operation.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed is:

1. A method implementable to a horticultural operation comprising one or more local areas, the method implemented by a system configured to autonomously interact with the horticultural operation, the method comprising:
    autonomously identifying the horticultural operation or a target located within the horticultural operation and an action to be performed with respect to the horticultural operation or target, the operation or target comprising at least one plant or a group of plants;
    determining, based on the identifying, a local area of the horticultural operation, wherein the target is located within the local area;
    associating the horticultural operation or target to at least one autonomous vehicle;
    locating, by the at least one autonomous vehicle, the horticultural operation or target within the local area; and
    performing the action with respect to the horticultural operation or target by the at least one autonomous vehicle by:
        determining a quantity of autonomous vehicles needed for performing a mission that includes the action;
        performing a resource check for autonomous vehicles until a number of autonomous vehicles equal to or exceeding the quantity pass the resource check, wherein the performing of the resource check is performed in parallel or begins with one of the autonomous vehicles that is located closest to the target and continues with others of the autonomous vehicles based on a distance between the respective autonomous vehicle and the target; and
        assigning the mission to the number of autonomous vehicles.

2. The method of claim 1, further comprising determining a path between the at least one autonomous vehicle and the local area, the path avoiding one or more restricted zones; wherein each of the one or more restricted zones is continuous and comprises at least a portion of the local area.

3. The method of claim 2, further comprising using 3D data to map obstacles.

4. The method of claim 2, wherein the one or more restricted zones comprises one of the following:
    a portion of the local area above a first altitude or below a second altitude;
    a portion of the local area at a ground level; or
    an identified object within the local area.

5. The method of claim 2, wherein the one or more restricted zones are determined based on one or more of the following:
    a custom master grower defined region;
    a height of a growing plant within a local area;
    a location of a physical structure;
    a local area currently having a horticultural activity;
    a passage reserved for ground traffic;
    an air corridor reserved for aerial traffic;
    an area in which flying is restricted by a regulation; or
    a weather condition.

6. The method of claim 1, further comprising:
    determining a set of sub-tasks and a corresponding quantity of autonomous vehicles needed for performing a mission;
    performing a resource check on available autonomous vehicles;
    dynamically assigning a sub-task to available autonomous vehicles that pass a resource check; and
    continuing to assign sub-tasks as autonomous vehicles become available until all sub-tasks of the set of sub-tasks have been completed.

7. The method of claim 1, wherein:
    the at least one autonomous vehicle is maneuvered based on one or more of GPS, GLONASS, RTK, inertial navigation, or visual odometry.

8. The method of claim 1, wherein:
    a plurality of beacons is disposed within the horticultural operation; and
    the beacons are located at defined 3D positions and emits a respective signal, the signal comprising a self-identifying RF signal, temporal or spatial visual patterns that can be captured by a camera, and wherein the signal is usable by an autonomous vehicle to determine a location or a path.

9. The method of claim 1, wherein QR identification devices are disposed in known positions within the horticultural operation, and the autonomous vehicles are configured to compute a position based on known positions of the QR identification devices.

10. The method of claim 1, wherein the local area comprises a plurality of plant units, wherein the target is a plant unit or a group of plant units, wherein each of the plant units or group of plant units is associated with a machine-readable code, and wherein the locating of the target within the local area comprises scanning the machine-readable code of the plant unit or group of plant units.

11. The method of claim 10, wherein the machine-readable code is used to define one or more boundaries of the local area and identify the local area.

12. The method of claim 1, wherein the action comprises collecting horticultural data pertinent to the target, the method further comprising one or more of:
    transmitting the horticultural data to a system for analysis after the action is performed; or
    performing the analysis on the autonomous vehicle.

13. The method of claim 1, wherein the action comprises collecting horticultural data pertinent to the target, the method further comprising one or more of:
    maneuvering the at least one autonomous vehicle to a data transfer bay after the action is performed and transferring the horticultural data collected by the at least one autonomous vehicle to a storage device located at the data transfer bay; or wirelessly transmitting the horticultural data to a data transfer station, a Wifi network, or to a cell tower.

14. The method of claim 13, wherein the horticultural data comprises one of the following:

a composite image of the target or an area surrounding the target;
an image of the target;
an estimated height of the target;
a mesh analysis of the target;
estimated volume of the target;
a temperature reading in a vicinity of the target;
a humidity reading in a vicinity of the target;
an illumination reading in a vicinity of the target;
a pH level of soil or water in which the target is planted;
a physical sample of the target;
a germination state of the target;
canopy coverage of the target;
canopy growth of the target;
flower/bud count of the target; or
disease or anomaly regions of the target.

15. The method of claim 13, further comprising determining that the target and only the target is in the horticultural data.

16. A system, comprising:

a vehicle bay hosting a plurality of autonomous vehicles
one or more processors;
memory having instructions stored therein, wherein the instructions, when executed by the one or more processors, cause the one or more processors to:
identify a horticultural operation or a target located within the horticultural operation and an action to be performed with respect to the horticultural operation or the target, the operation or target comprising at least one plant or a group of plants;
determine, based on the identification, a local area of the operation or target;
assign the target to at least one autonomous vehicle of the plurality of autonomous vehicles;
locate, by the at least one autonomous vehicle based on the identification, the local area; and
perform the action with respect to the operation or target by the at least one autonomous vehicle by:
determining a quantity of autonomous vehicles needed for performing a mission that includes the action;
performing a resource check for autonomous vehicles until a number of autonomous vehicles equal to or exceeding the quantity pass the resource check, wherein the performing of the resource check is performed in parallel or begins with one of the autonomous vehicles that is located closest to the target and continues with others of the autonomous vehicles based on a distance between the respective autonomous vehicle and the target; and
assigning the mission to the number of autonomous vehicles.

17. The system of claim 16, further comprising a plurality of cameras disposed across the horticultural operation, each of the plurality of cameras capable of monitoring one or more of the local areas and providing image data to the autonomous vehicles or the system.

* * * * *